(12) United States Patent
Abrams et al.

(10) Patent No.: US 12,594,271 B2
(45) Date of Patent: Apr. 7, 2026

(54) COMBINATION THERAPY FOR CANCER

(71) Applicant: Health Research, Inc., Buffalo, NY (US)

(72) Inventors: Scott I. Abrams, Amherst, NY (US); Sean H. Colligan, Buffalo, NY (US)

(73) Assignee: Health Research, Inc., Buffalo, NY (US)

( * ) Notice: Subject to any disclaimer, the term of this patent is extended or adjusted under 35 U.S.C. 154(b) by 919 days.

(21) Appl. No.: 17/773,838

(22) PCT Filed: Nov. 5, 2020

(86) PCT No.: PCT/US2020/059131
§ 371 (c)(1),
(2) Date: May 2, 2022

(87) PCT Pub. No.: WO2021/092190
PCT Pub. Date: May 14, 2021

(65) Prior Publication Data
US 2022/0395494 A1 Dec. 15, 2022

Related U.S. Application Data

(60) Provisional application No. 63/075,634, filed on Sep. 8, 2020, provisional application No. 62/930,828, filed on Nov. 5, 2019.

(51) Int. Cl.
*A61K 31/47* (2006.01)
*A61K 31/4353* (2006.01)
(Continued)

(52) U.S. Cl.
CPC .......... *A61K 31/47* (2013.01); *A61K 31/4353* (2013.01); *A61P 35/00* (2018.01); *A61K 39/00* (2013.01)

(58) Field of Classification Search
CPC .... A61K 31/47; A61K 31/4353; A61K 39/00; A61P 35/00
See application file for complete search history.

(56) References Cited

U.S. PATENT DOCUMENTS 8,614,301 B2 12/2013 Arber
2015/0118222 A1 4/2015 Levy et al.
(Continued)

FOREIGN PATENT DOCUMENTS

WO 2017197140 A1 11/2017
WO 2018136009 A1 7/2018
WO 2019090244 A2 5/2019

OTHER PUBLICATIONS

Dorasamy, Mathura Subangari, et al. "Synergistic inhibition of melanoma xenografts by Brequinar sodium and Doxorubicin." Biomedicine & Pharmacotherapy 110 (2019): 29-36. (Year: 2019).*
(Continued)

*Primary Examiner* — James H Alstrum-Acevedo
*Assistant Examiner* — Justin Christopher Sanchez
(74) *Attorney, Agent, or Firm* — Hodgson Russ LLP

(57) ABSTRACT

Provided are methods for treatment of cancer. The method comprises administering to an individual who has cancer a combination of treatment to reduce MDSC burden and immune therapy. For example, an individual may be administered brequinar and an immune checkpoint inhibitor. This disclosure provides a method for redirecting early myeloid precursors away from generating MDSCs thereby reducing MDSC burden.

6 Claims, 24 Drawing Sheets

(51) Int. Cl.
*A61K 39/00* (2006.01)
*A61P 35/00* (2006.01)

(56) References Cited

U.S. PATENT DOCUMENTS

| | | |
|---|---|---|
| 2018/0078628 A1 | 3/2018 | Antonia et al. |
| 2018/0193342 A1 | 7/2018 | Gandhi et al. |

OTHER PUBLICATIONS

Burris, H.A., Raymond, E., Awada, A. et al. Pharmacokinetic and phase I studies of brequinar (DUP 785; NSC 368390) in combination with cisplatin in patients with advanced malignancies. Invest New Drugs 16, 19â27 (1998) (Year: 1998).*

American Cancer Society. "Breast Cancer Risk and Prevention". https://www.cancer.org/content/dam/CRC/PDF/Public/8578.00. pdf. Accessed Apr. 29, 2025. (Year: 2025) (Year: 2025).*

DrugBank. "Brequinar". https://go.drugbank.com/drugs/DB03523, Published Oct. 21, 2005. Accessed Apr. 29, 2025 (Year: 2005).*

Jia, Hongyan, et al. "Immunotherapy for triple-negative breast cancer: Existing challenges and exciting prospects." Drug resistance updates 32 (2017): 1-15. (Year: 2017).*

Shou, Dawei, et al. "Suppressive role of myeloid-derived suppressor cells (MDSCs) in the microenvironment of breast cancer and targeted immunotherapies." Oncotarget 7.39 (2016): 64505. (Year: 2016).*

Stahl et al., "Immune Checkpoint Inhibitors in Acute Myeloid Leukemia: Novel Combinations and Therapeutic Targets," Current Oncology Reports, Mar. 23, 2019, pp. 1-10, vol. 21, No. 37.

Tobin et al., "Targeting myeloid-derived suppressor cells using all-trans retinoic acid in melanoma patients treated with Ipilimumab," International Immunopharmacology, Aug. 16, 2018, pp. 282-291, vol. 63.

Sainas et al., "Targeting Myeloid Differentiation Using Potent 2-Hydroxypyrazolo [1,5-a ] pyridine Scaffold-Based Human Dihydroorotate Dehydrogenase Inhibitors," Journal of Medicinal Chemistry, Jun. 25, 2018, pp. 6034-6055, vol. 61, No. 14.

* cited by examiner

A
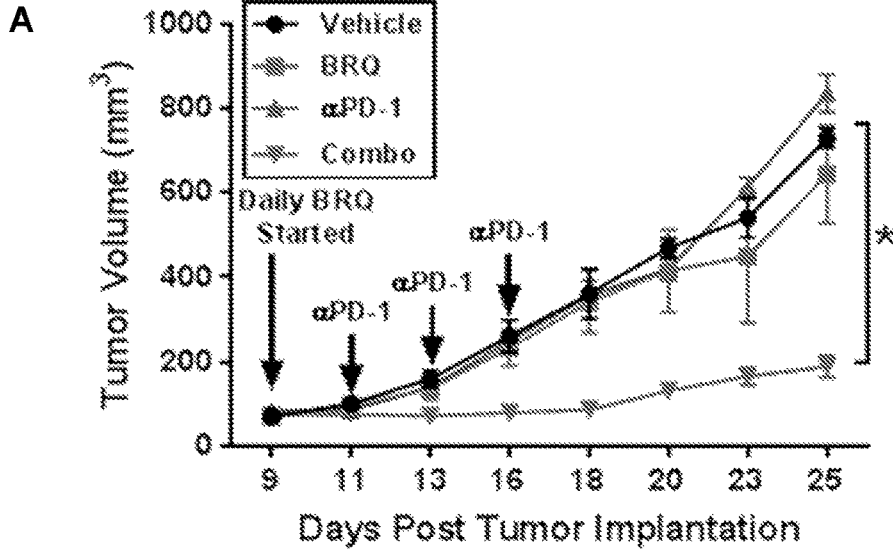
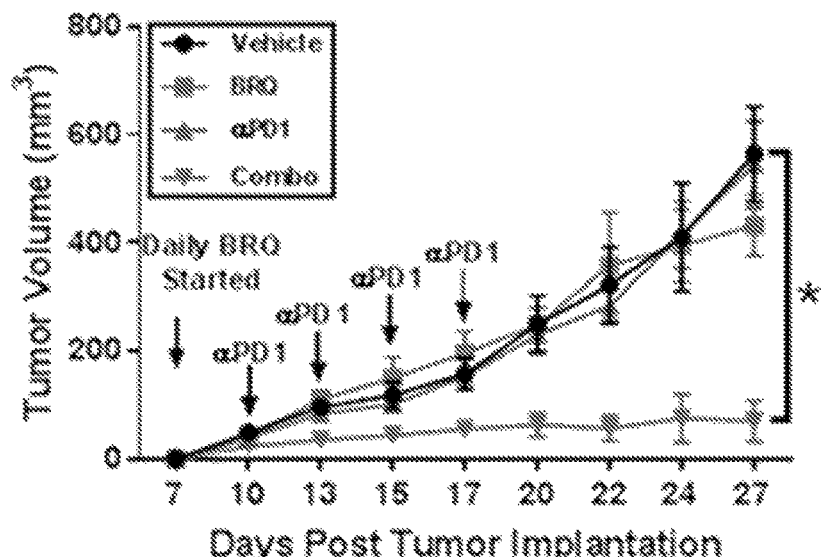
B
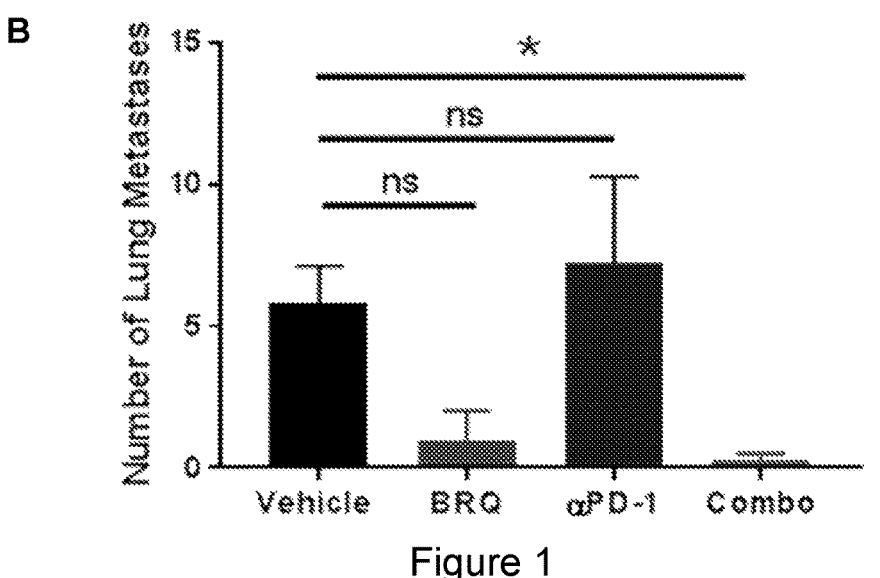
Figure 1

C
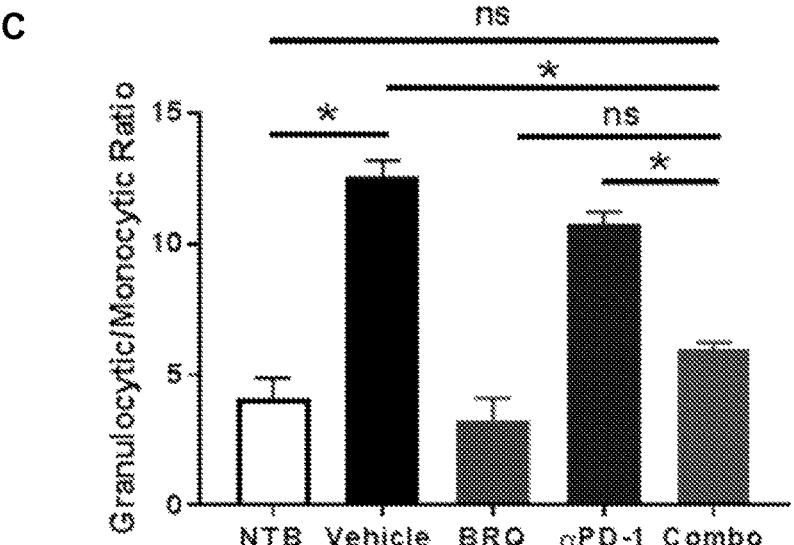
D
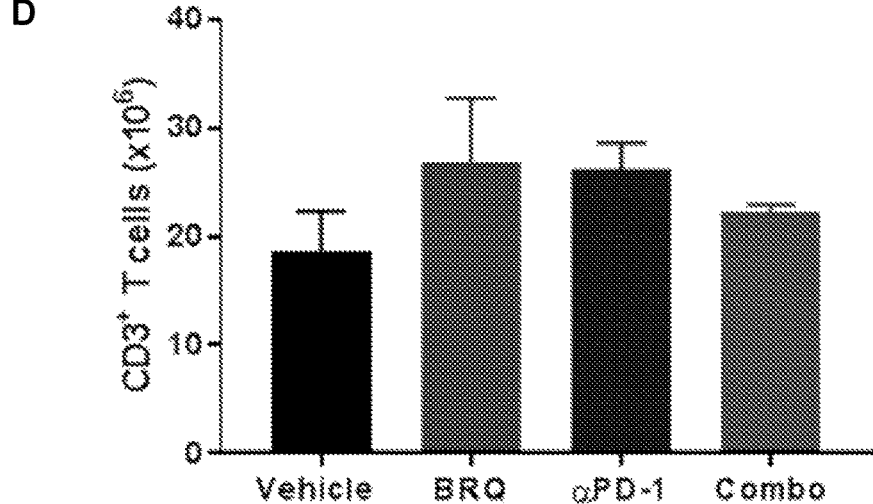
E
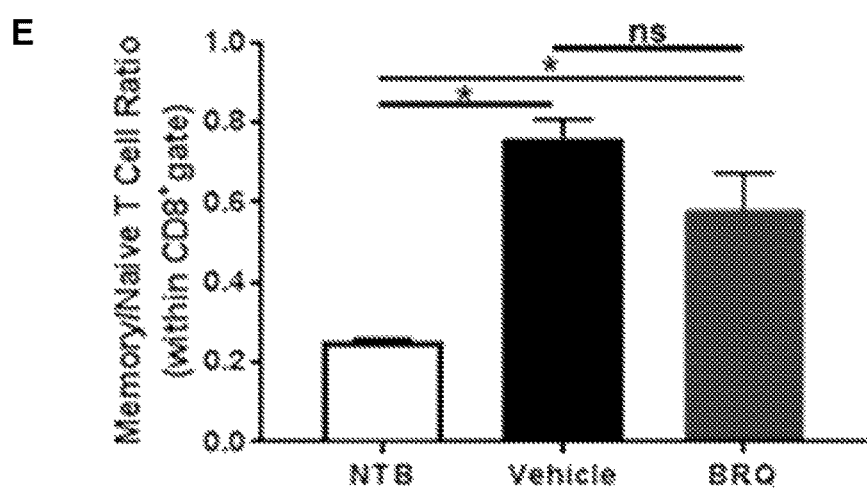
Figure 1 (continued)

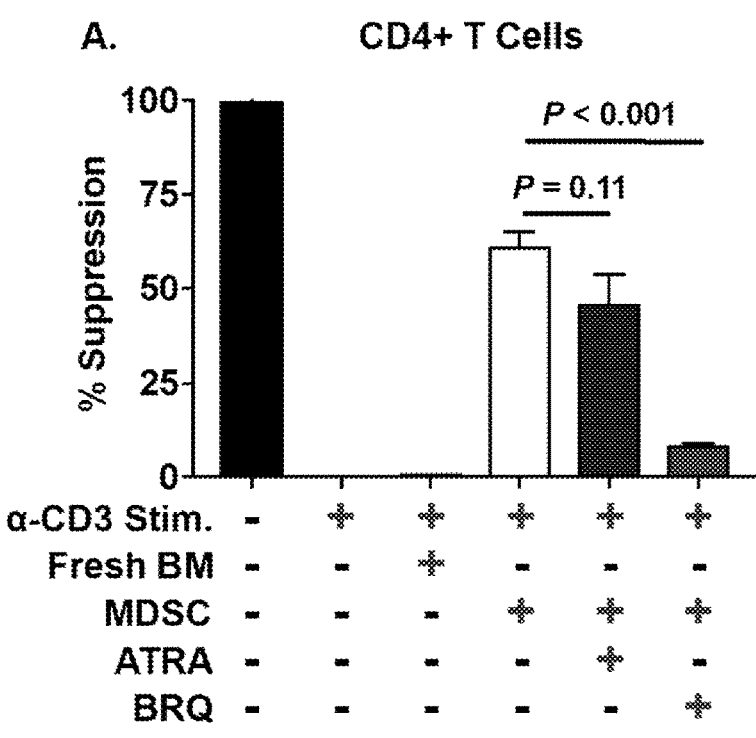
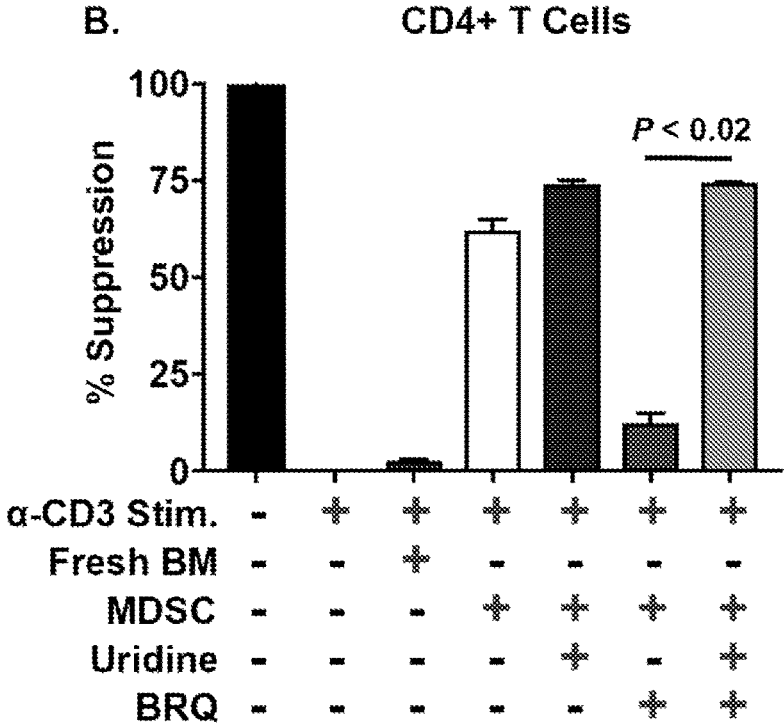
Figure 2

C.

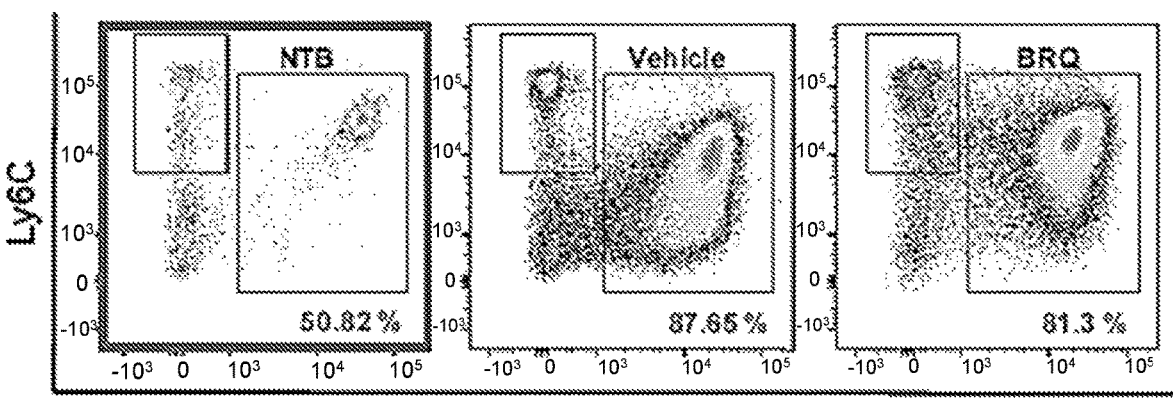
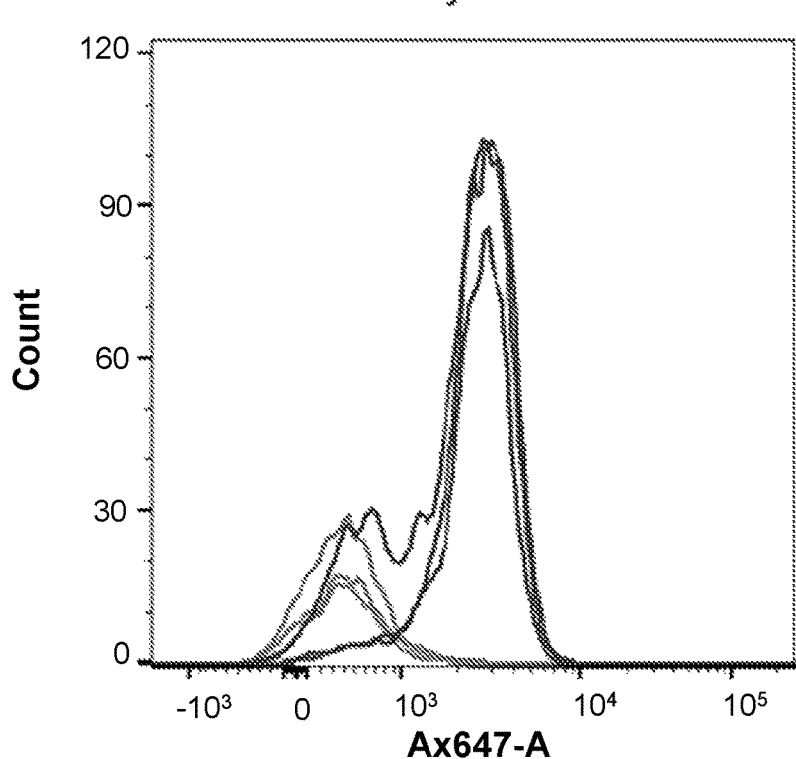
| | Sample Name | Subset Name | Median : Ax647-A |
|---|---|---|---|
| ☐ | Specimen_001_WT 3_004.fcs | Granulocytes | 2644 |
| ☐ | Specimen_001_WT 2_003.fcs | Granulocytes | 2718 |
| ☐ | Specimen_001_WT 1_002.fcs | Granulocytes | 2341 |
| ☐ | Specimen_001_WT 3_004.fcs | Monocytes | 392 |
| ☐ | Specimen_001_WT 2_003.fcs | Monocytes | 458 |
| ☐ | Specimen_001_WT 1_002.fcs | Monocytes | 403 |
Figure 14

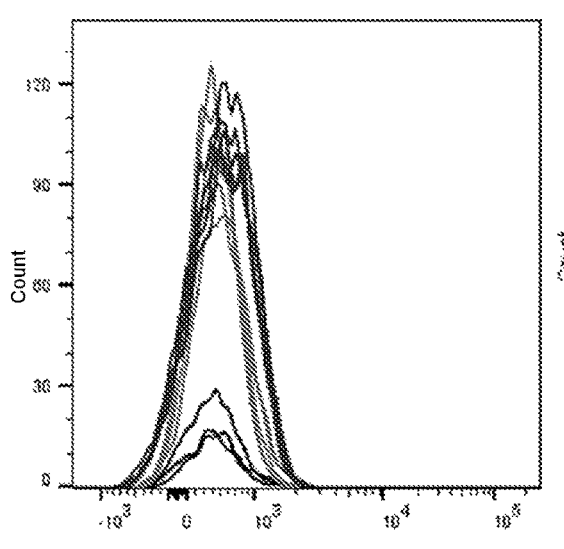

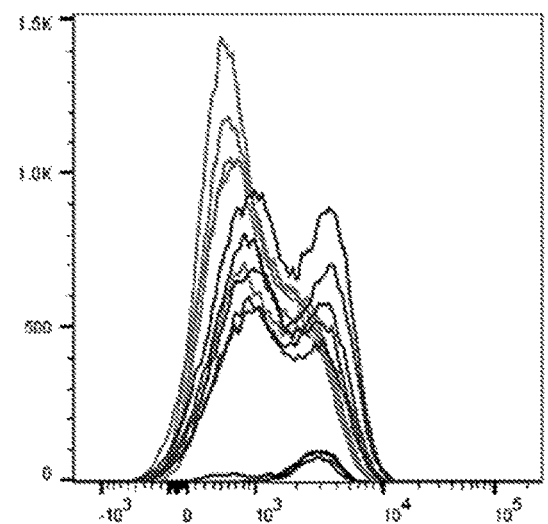

| Sample Name | Subset Name | Median : Ax647-A |
|---|---|---|
| Specimen_001_BRQ 5_014.fcs | Monocytes | 553 |
| Specimen_001_BRQ 4_013.fcs | Monocytes | 610 |
| Specimen_001_BRQ 3_012.fcs | Monocytes | 615 |
| Specimen_001_BRQ 2_011.fcs | Monocytes | 527 |
| Specimen_001_BRQ 1_010.fcs | Monocytes | 631 |
| Specimen_001_NT 5_009.fcs | Monocytes | 421 |
| Specimen_001_NT 4_008.fcs | Monocytes | 390 |
| Specimen_001_NT 3_007.fcs | Monocytes | 444 |
| Specimen_001_NT 2_006.fcs | Monocytes | 556 |
| Specimen_001_NT 1_005.fcs | Monocytes | 399 |
| Specimen_001_WT 3_004.fcs | Monocytes | 382 |
| Specimen_001_WT 2_003.fcs | Monocytes | 458 |
| Specimen_001_WT 1_002.fcs | Monocytes | 460 |

| Sample Name | Subset Name | Median : Ax647-A |
|---|---|---|
| Specimen_001_BRQ 5_014.fcs | Granulocytes | 1402 |
| Specimen_001_BRQ 4_013.fcs | Granulocytes | 1213 |
| Specimen_001_BRQ 3_012.fcs | Granulocytes | 1264 |
| Specimen_001_BRQ 2_011.fcs | Granulocytes | 1379 |
| Specimen_001_BRQ 1_010.fcs | Granulocytes | 1478 |
| Specimen_001_NT 5_009.fcs | Granulocytes | 892 |
| Specimen_001_NT 4_008.fcs | Granulocytes | 688 |
| Specimen_001_NT 3_007.fcs | Granulocytes | 892 |
| Specimen_001_NT 2_006.fcs | Granulocytes | 1170 |
| Specimen_001_NT 1_005.fcs | Granulocytes | 779 |
| Specimen_001_WT 3_004.fcs | Granulocytes | 2644 |
| Specimen_001_WT 2_003.fcs | Granulocytes | 3718 |
| Specimen_001_WT 1_002.fcs | Granulocytes | 2341 |

Granulocyte CD101 Expression

%CD101$^{hi}$ Cells

Figure 15

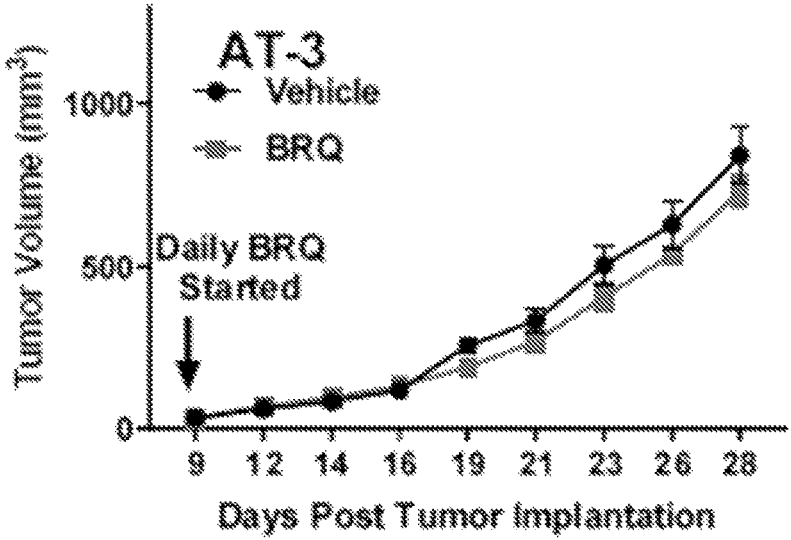
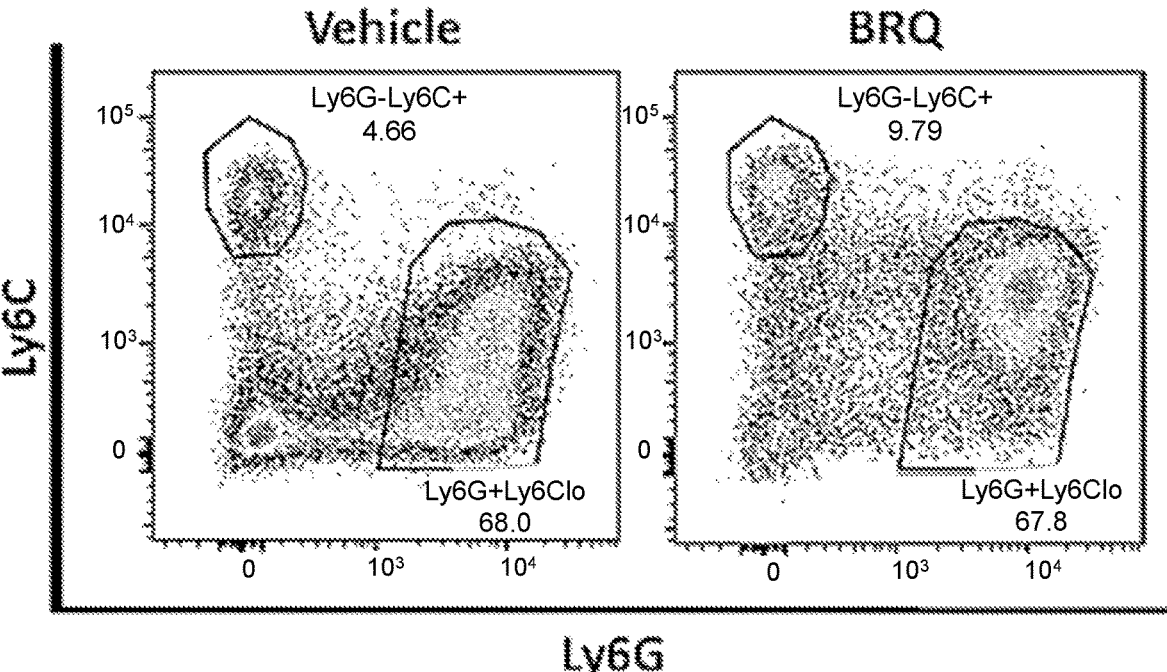
Figure 16

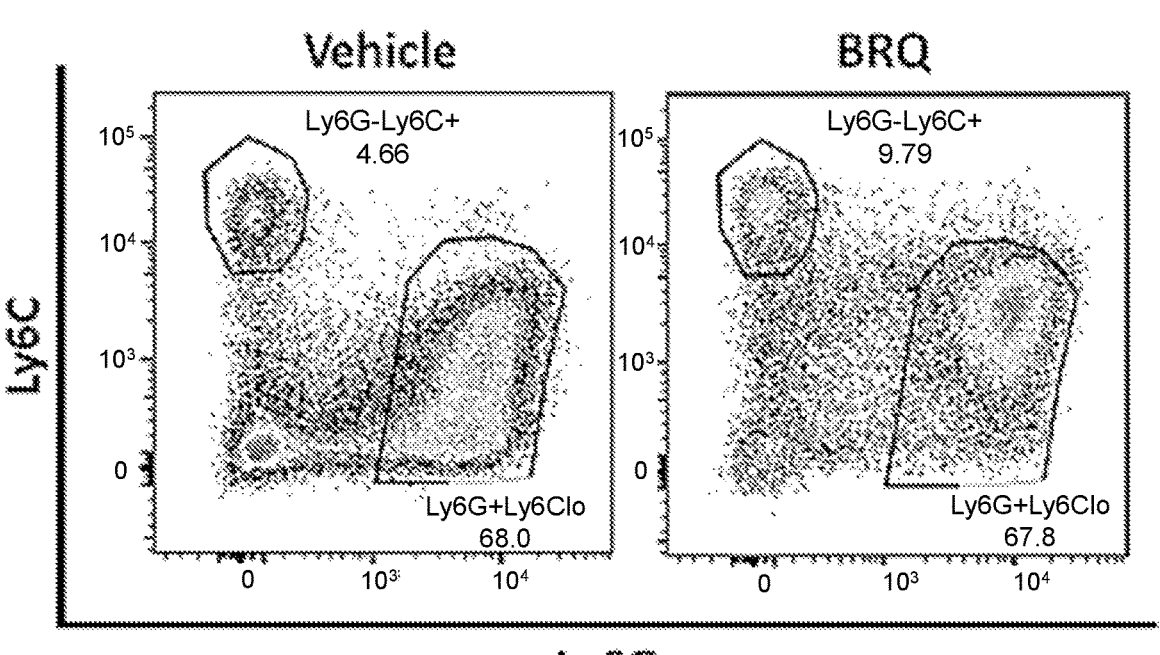
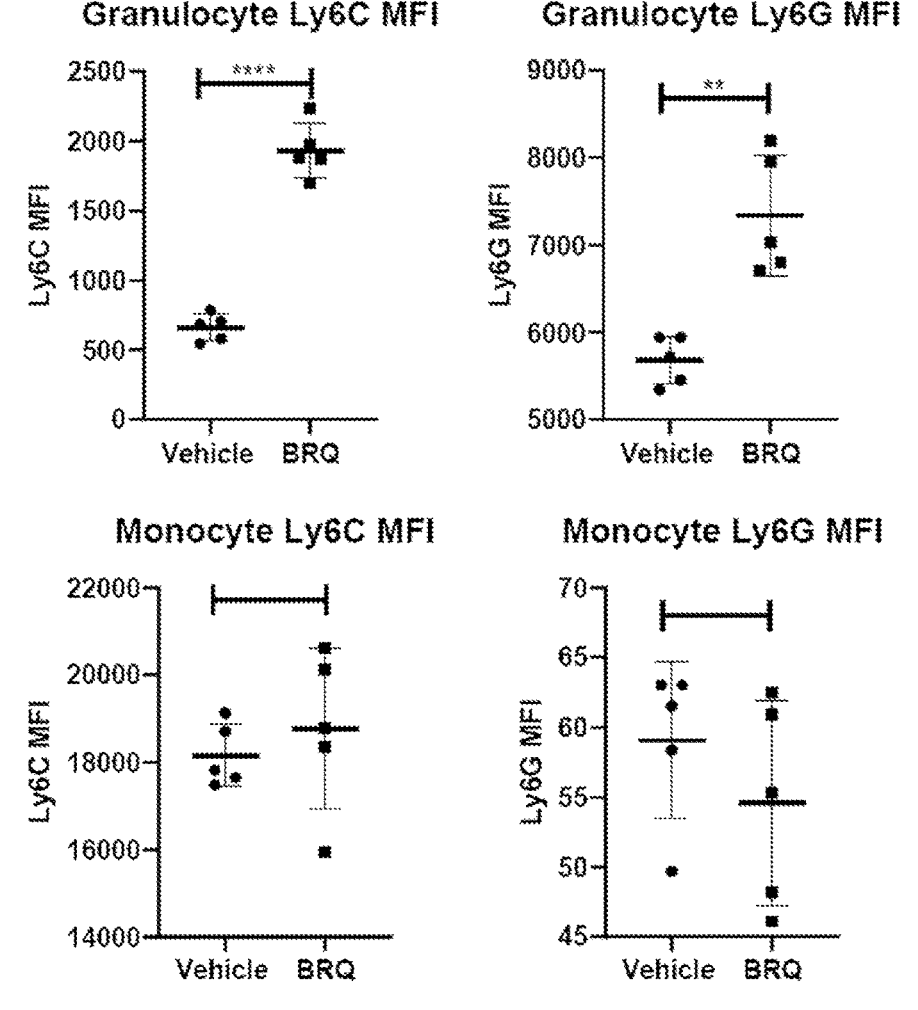
Figure 17

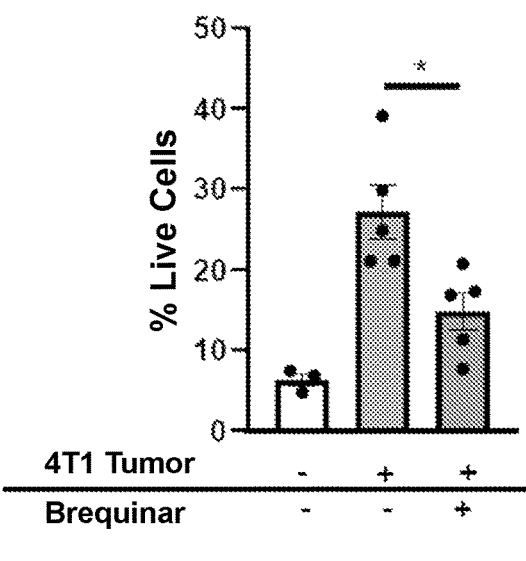
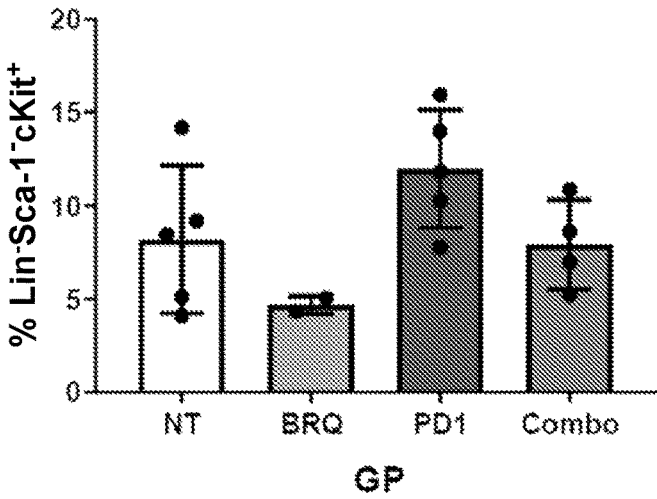
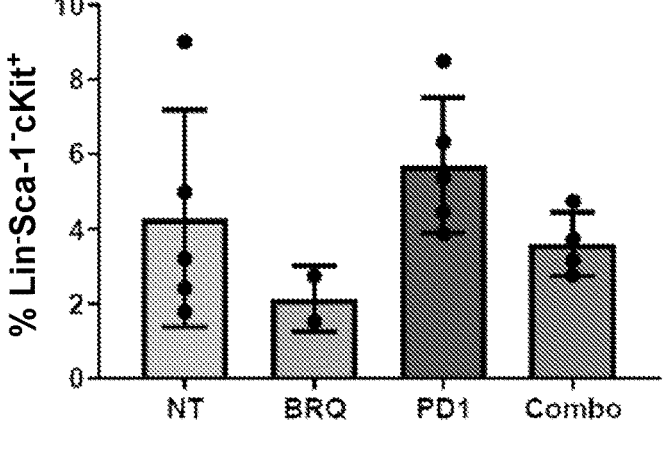
Figure 19

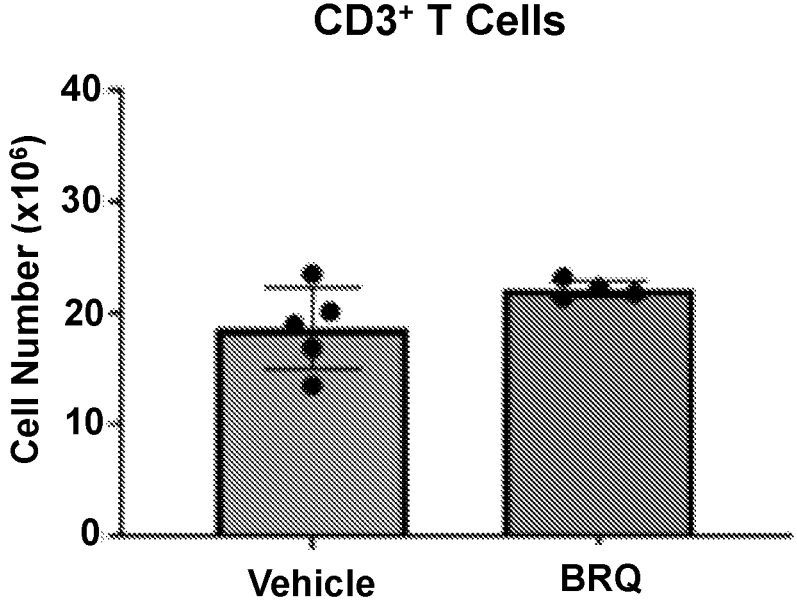
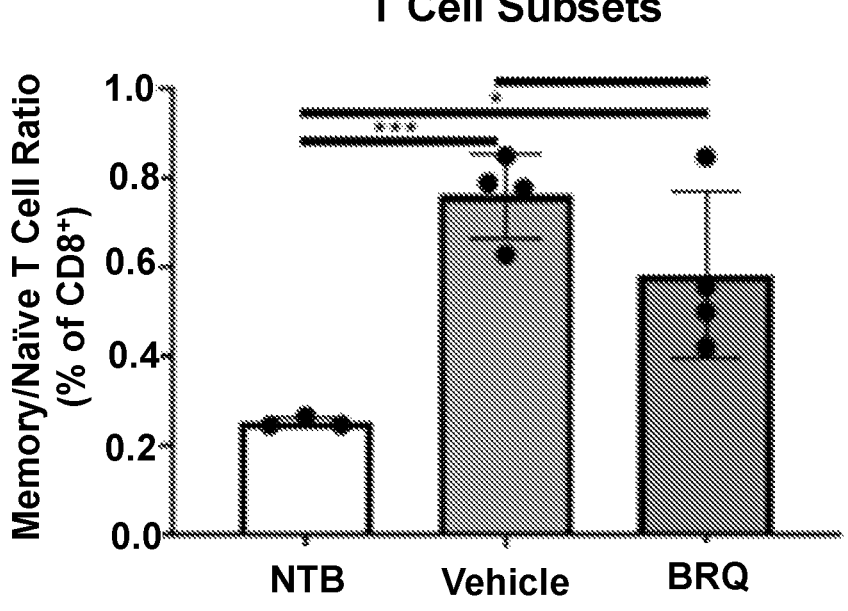
Figure 20

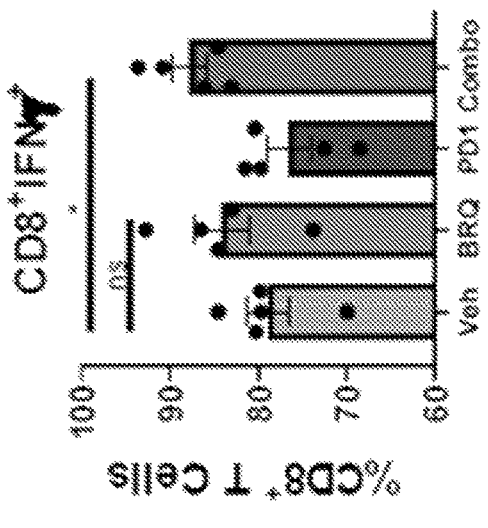
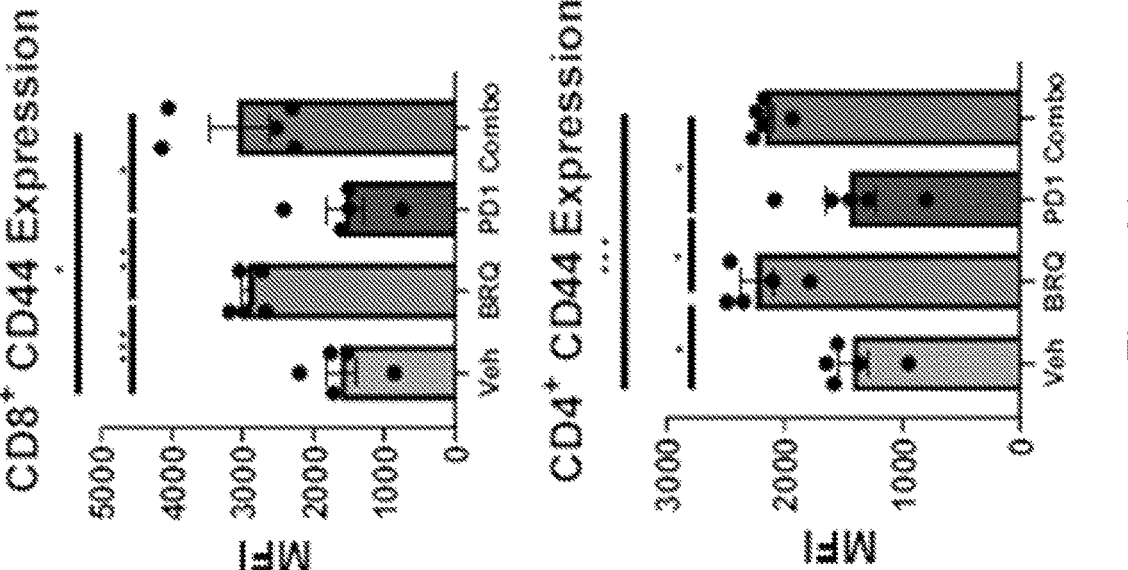
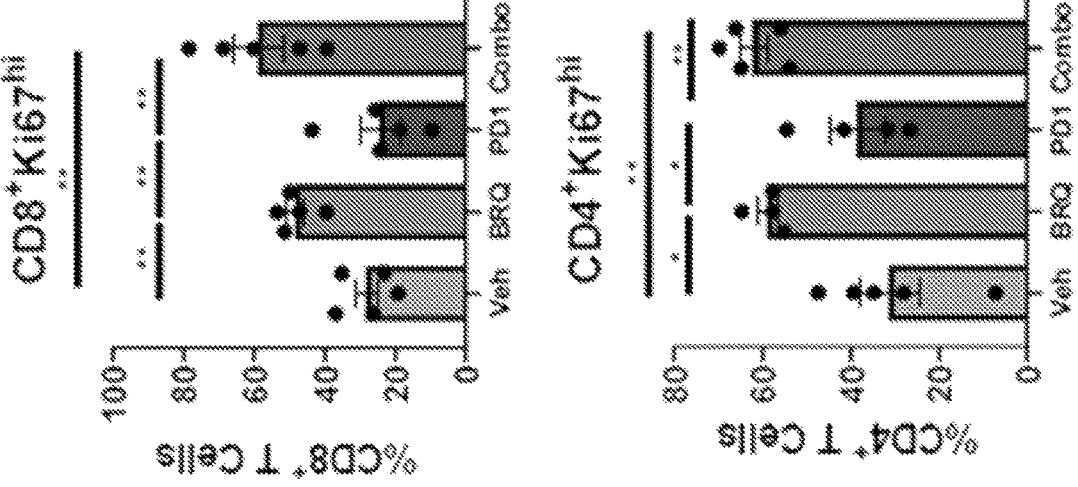
Figure 21

1

COMBINATION THERAPY FOR CANCER

CROSS-REFERENCE TO RELATED APPLICATIONS

This application claims priority to U.S. Provisional patent application No. 62/930,828, filed on Nov. 5, 2019, and to U.S. Provisional patent application No. 63/075,634, filed on Sep. 8, 2020, the disclosures of each of which are incorporated herein by reference.

STATEMENT REGARDING FEDERALLY-SPONSORED RESEARCH OR DEVELOPMENT

This invention was made with government support under grant numbers R01CA172105 and F31CA228396 awarded by the National Institutes of Health. The government has certain rights in the invention.

BACKGROUND OF THE DISCLOSURE

The immune system plays key roles in tumor progression and response to treatment. Multiple therapeutic strategies, including immune checkpoint inhibitors, target the immune system. Yet, none of the current immune-targeted strategies are particularly effective for treating most solid cancers.

All immune cells arise in the bone marrow through a tightly coordinated and regulated process. Altered hematopoiesis, particularly affecting the myeloid system, occurs in cancer patients and in mouse tumor models. A key feature of altered myeloid differentiation is an increased frequency of immature cells that possess immune suppressive properties, termed myeloid-derived suppressor cells (MDSCs). MDSCs not only suppress protective immune cells, but directly promote cancer progression and tumor growth, and can hinder patient responses to anti-tumor immunotherapy. A strategy through which to target MDSCs therapeutically in the clinic is differentiation therapy, which could enforce MDSCs to fully mature into healthy myeloid cells, thereby depleting MDSCs from the tumor site. However, current therapies aimed at promoting MDSC differentiation have shown limited clinical success. As such, there is a continuing need to identify approaches that will effectively deplete the MDSC population.

SUMMARY OF THE DISCLOSURE

This disclosure provides a method for redirecting early myeloid precursors away from generating MDSCs thereby reducing MDSC burden. It is considered that in cancer, MDSCs may be arrested at immature states thereby acquiring immune suppressive, rather than immune activating. By redirecting early myeloid precursors away from MDSCs, the present disclosure provides a method for treatment of cancer.

In an aspect, this disclosure provides a method for treatment of cancer comprising administering to an individual in need of treatment, an agent which reduces MDSC burden, alone or in combination with another anti-cancer therapy. The anticancer therapy used in combination with reducing MDSC burden may be an immune checkpoint inhibitor. The agent for reducing MDSCs may be Brequinar (BRQ) or another DHODH inhibitor. In an embodiment, the method comprises administering to an individual in need of treatment BRQ and an anti-PD-1.

BRIEF DESCRIPTION OF THE DRAWINGS

FIG. 1. BRQ plus anti-PD-1 inhibits tumor growth. (A) 4T1 growth in mice treated daily with BRQ (10 mg/kg, i.p.), anti-PD-1 (200 µs, i.p. at the indicated 3 or 4 times) or both agents. n=5 mice/group/experiment for upper and lower graphs; *P<0.01 against single-agent treatments. B-D, data shown are for analysis of A, upper graph. (B) Spontaneous metastatic lung counts; *P<0.01. Similar patterns seen in the $2^{nd}$ experiment (avg. #mets): vehicle=12; BRQ=1; αPD-1=5; combo=1. (C) Splenic granulocytic ($CD11b^+$ $Ly6C^{lo}Ly6G^+$) or monocytic ($CD11b^+Ly6C^{hi}Ly6G^-$) numbers in non-tumor-bearing (NTB) or tumor-bearing mice were converted to a ratio for group-by-group comparison; *P<0.03. (D) Splenic $CD3^+$ T cell numbers in tumor-bearing mice. (E) Splenic $CD8^+$ T cells in A (lower graph) were assayed based on differential expression of CD44:naïve (10) vs. effector/central memory (hi) phenotypes. *P<0.03. Data reported as a ratio to indicate a rising memory pool. Data in B-E are at endpoint; ns, not significant.

Figure 2:
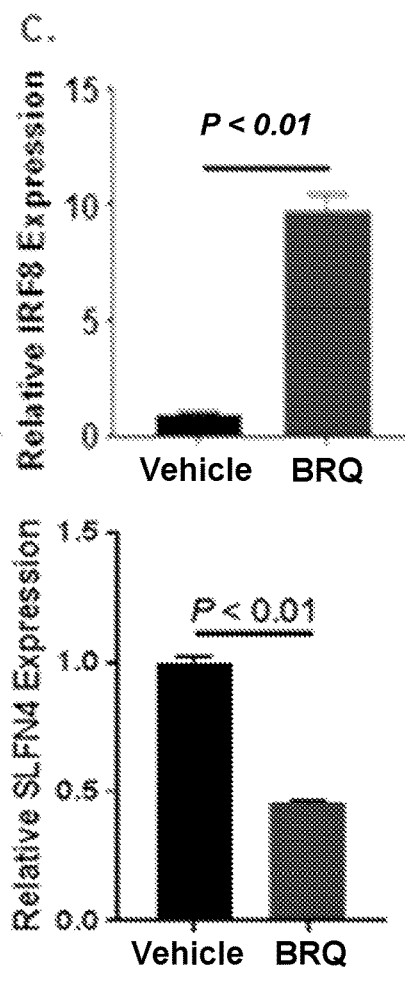

FIG. 2. BRQ inhibits MDSC-mediated immune suppression in vitro. (A) MDSCs were produced in vitro from mouse bone marrow cells using GM-CSF and G-CSF±BRQ (1 µM) or ATRA (10 µM) at the start of the 4-day culture. Cells tested for their ability to inhibit T cell proliferation (1:1 ratio), as in FIG. 5. Fresh BM=Uncultured bone marrow cells. (B) Similar to A, except that uridine (200 µM) was added to rescue the effect of BRQ. (C) Expression of IRF8 (upper) or SLFN4 (lower) was analyzed by qRT-PCR in $Lin^-$ BM cells cultured as in A for 2 days. Data normalized to the vehicle.

Figure 3:
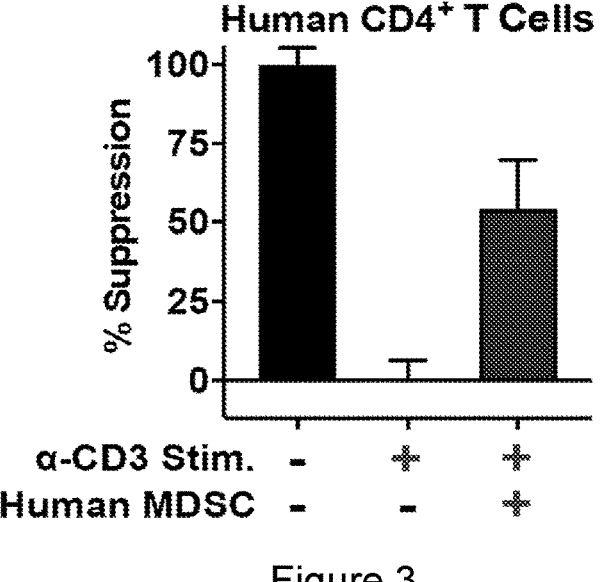

FIG. 3. Generation of MDSC activity from human bone marrow cultures. Unfractionated bone marrow cells from a healthy donor were cultured with G-GSF+GM-CSF. Suppression was assessed by inhibition of T cell proliferation by MDSCs (1:1 ratio).

Figure 4:
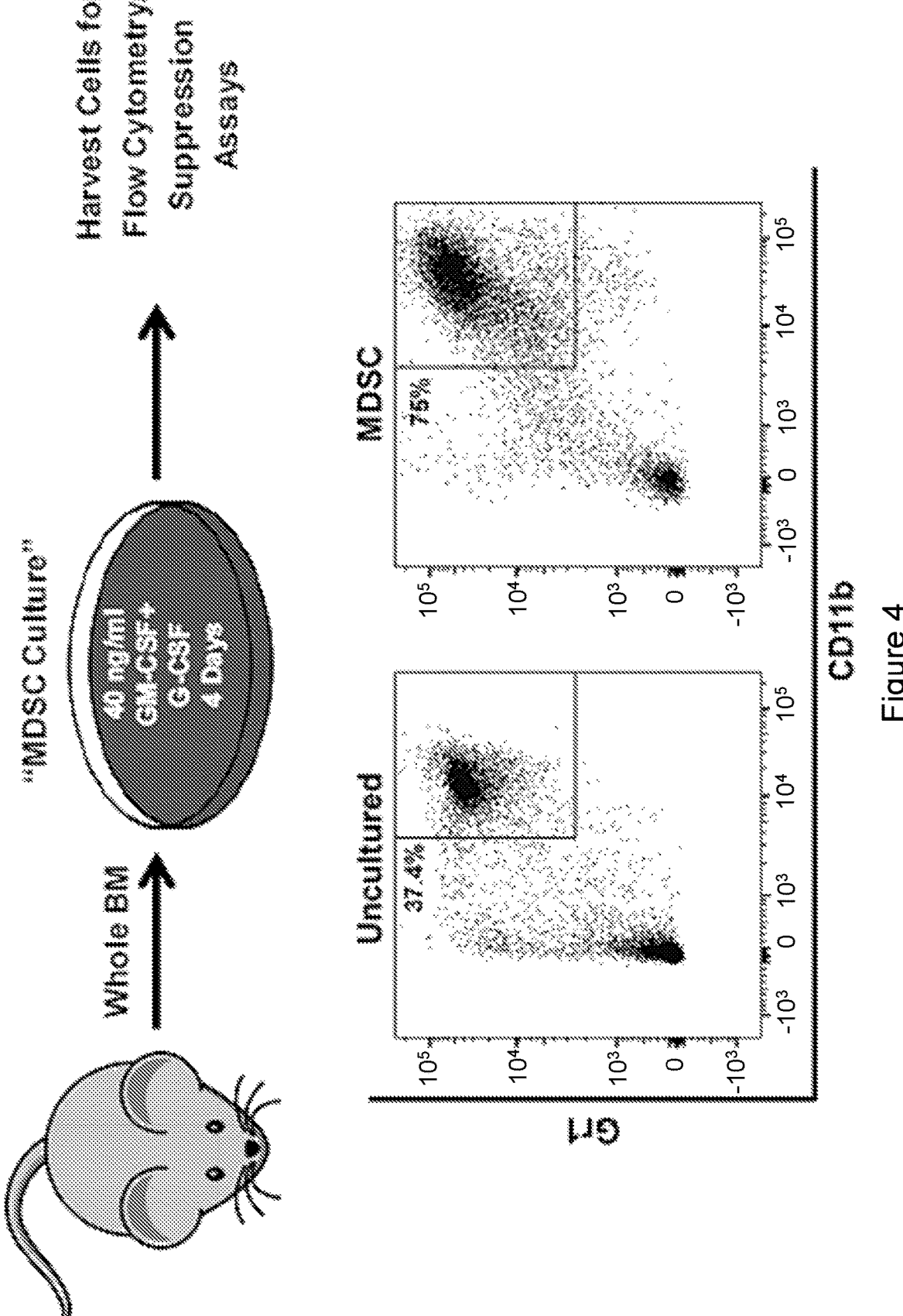

FIG. 4. In Vitro Development of MDSCs. Unfractionated mouse bone marrow cells were cultured in dishes with recombinant mouse G-CSF and recombinant mouse GM-CSF to produce MDSCs. Cells were collected and analyzed by flow cytometry for the CD11b cell surface marker. Uncultured or fresh bone marrow (BM) cells served as a negative control.

Figure 5:
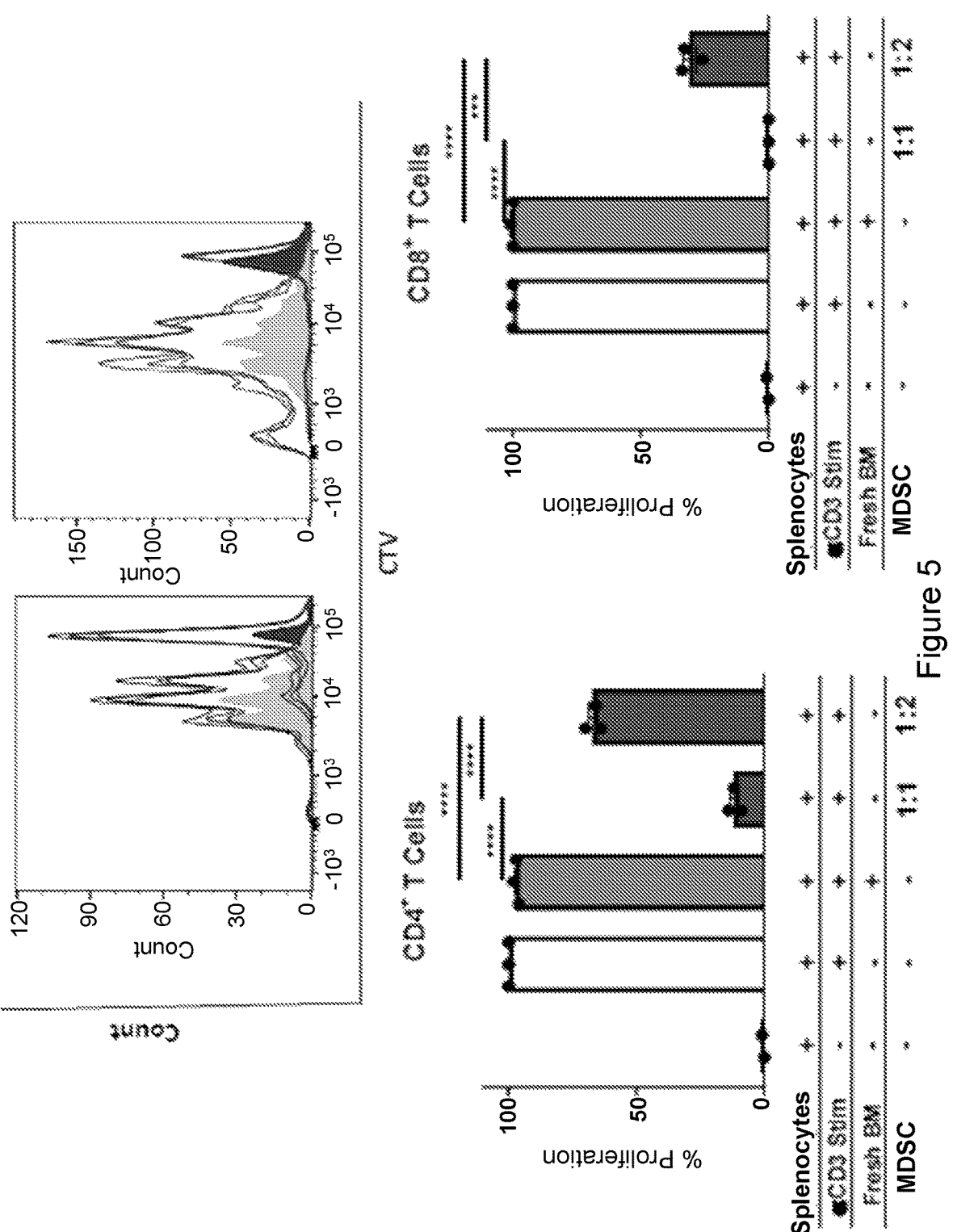

FIG. 5. Cultured Cells Develop Potent Immunosuppressive Capacity. Fresh BM (i.e., no in vitro culture) or cultured BM cells (i.e., MDSCs at two different MDSC-to-T cell ratios of 1:1 or 1:2) were co-mixed in 96-well plates with CellTrace Violet (CTV)—stained syngeneic naïve splenocytes as a source of T cells and stimulated with or without soluble agonistic anti-CD3 monoclonal antibody (mAb) (1 µg/ml) for 72 hours. After co-culture, CTV dye dilution in the gated $CD4^+$ or $CD8^+$ T cell fractions was analyzed by flow cytometry.

Figure 6:
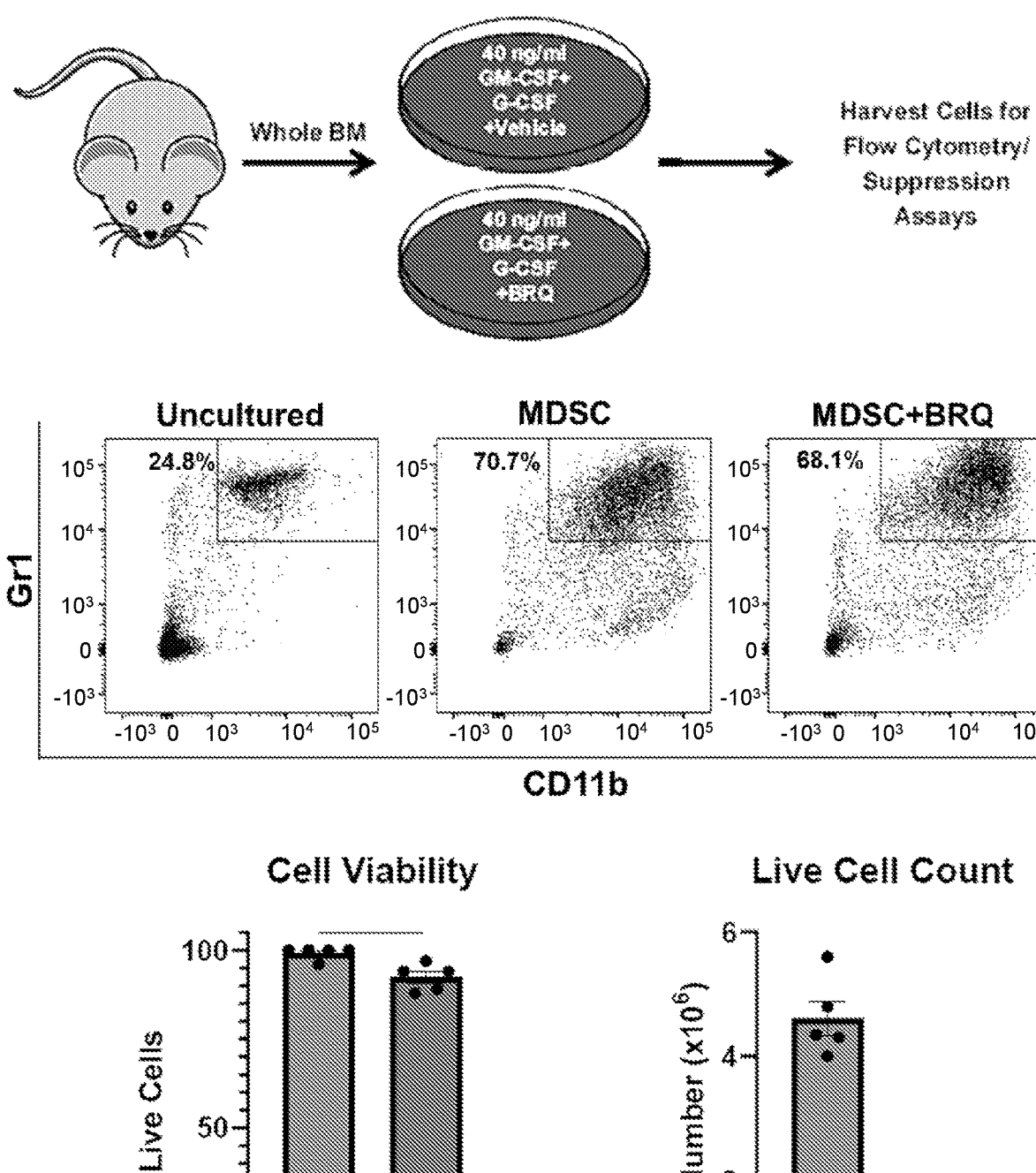

FIG. 6. Effect of BRQ Treatment on In Vitro Generated MDSCs. MDSCs were generated in vitro, but now with or without (vehicle) the concurrent addition of brequinar (BRQ) (1 µM) at the start of the culture. After culture, cells were collected and analyzed by flow cytometry for the indicated cell surface markers. Uncultured (fresh) BM cells served as a negative control. Viable cells were enumerated by trypan blue dye exclusion (bottom left panel, % viability; bottom right panel, total viable cells recovered).

Figure 7:
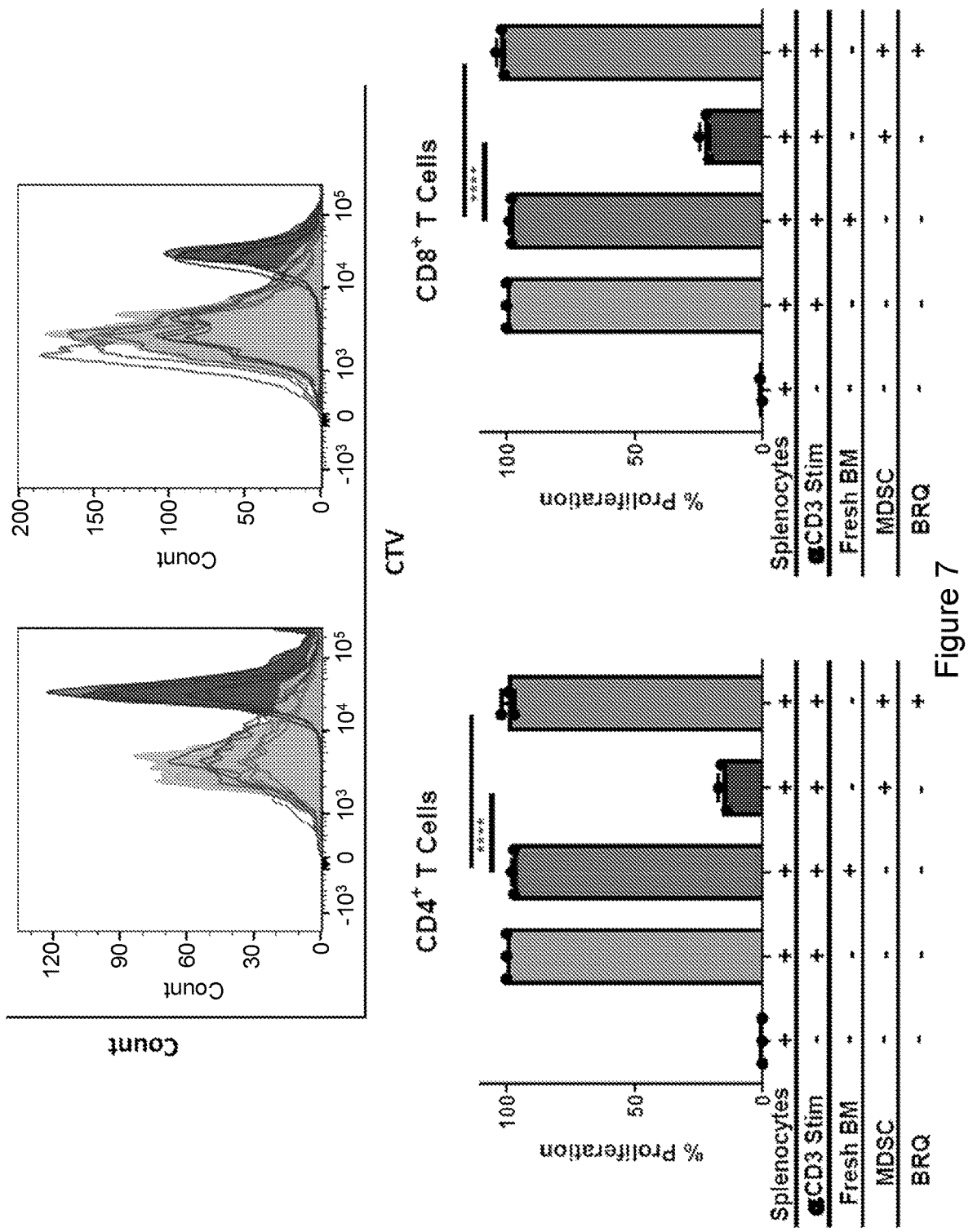

FIG. 7. BRQ Treatment Significantly Reverses the Immune Suppressive Capacity of MDSCs. Suppression assay and the methods used to analyze T cell proliferation were the same as in FIG. 5, except that an additional group with BRQ (1 µM) was included, as described in the experiment for FIG. 6. Cells were assayed for their ability to inhibit T cell proliferation.

Figure 8:
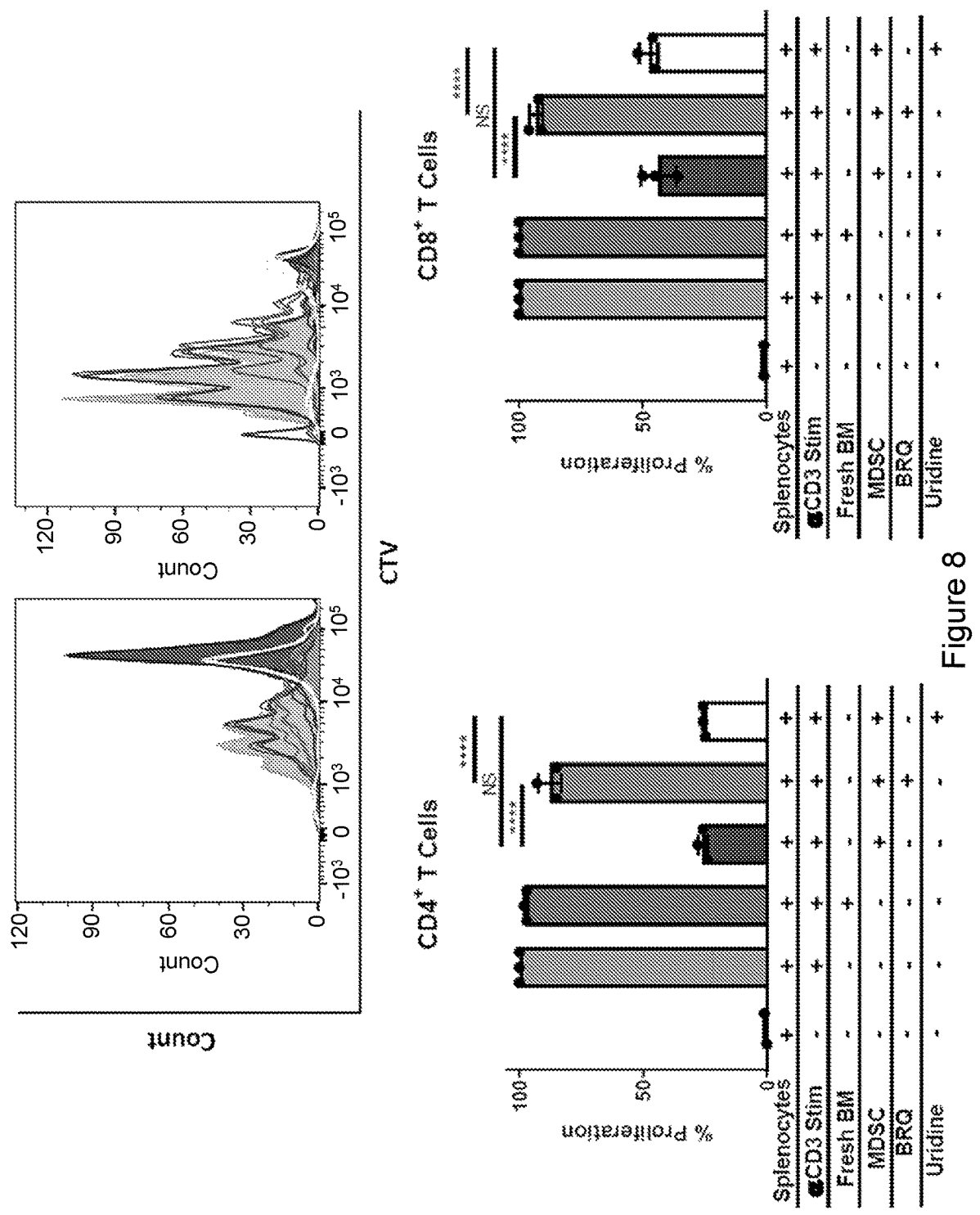

FIG. 8. Supplementation with Uridine Rescues the Effects of BRQ Treatment. Suppression assay and the methods used to analyze T cell proliferation were the same as described above, except that an additional group with BRQ (1 µM) plus extracellular uridine (200 µM) was included. NS refers to not significant.

Figure 9:
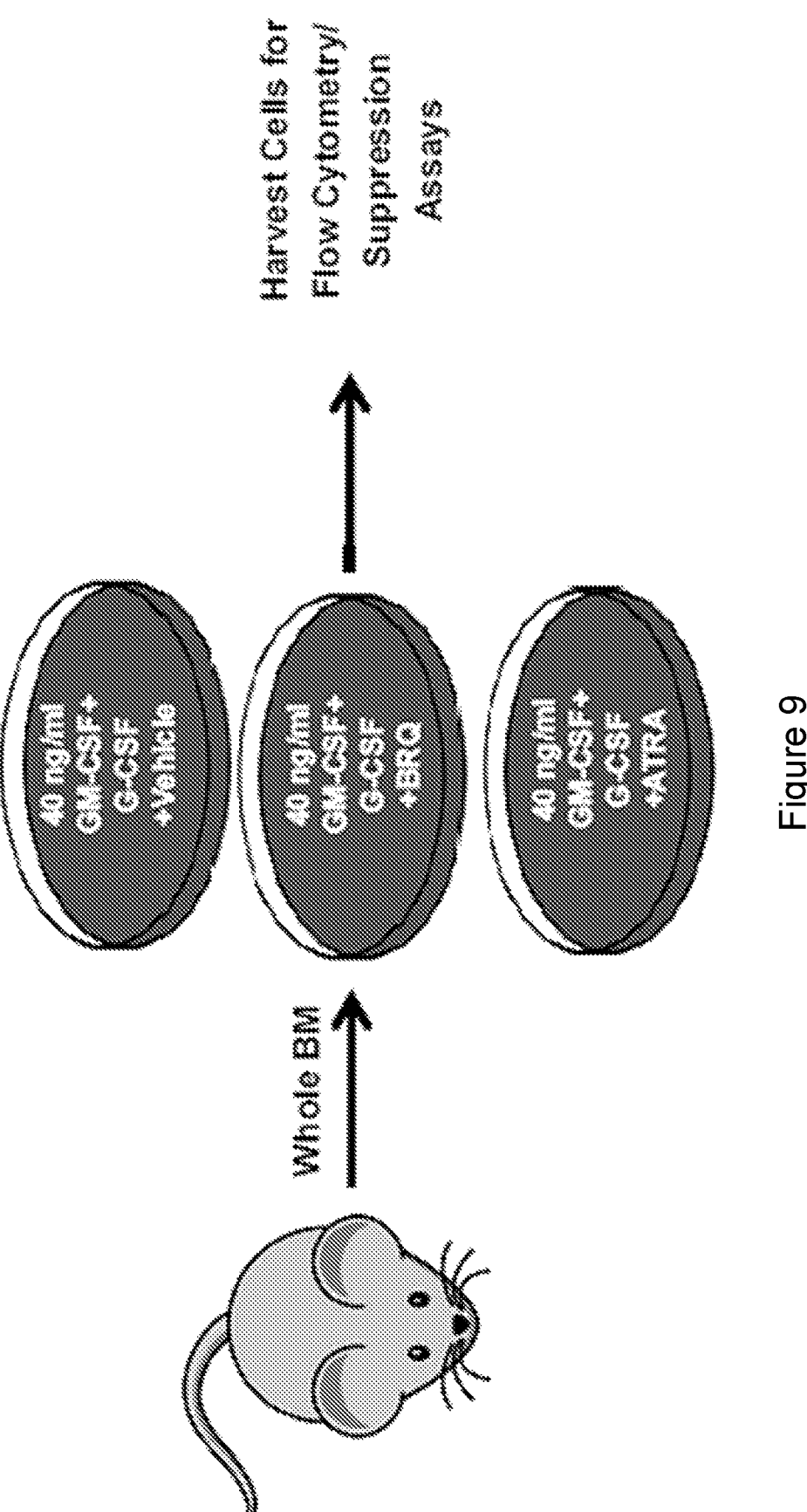
Figure 10:
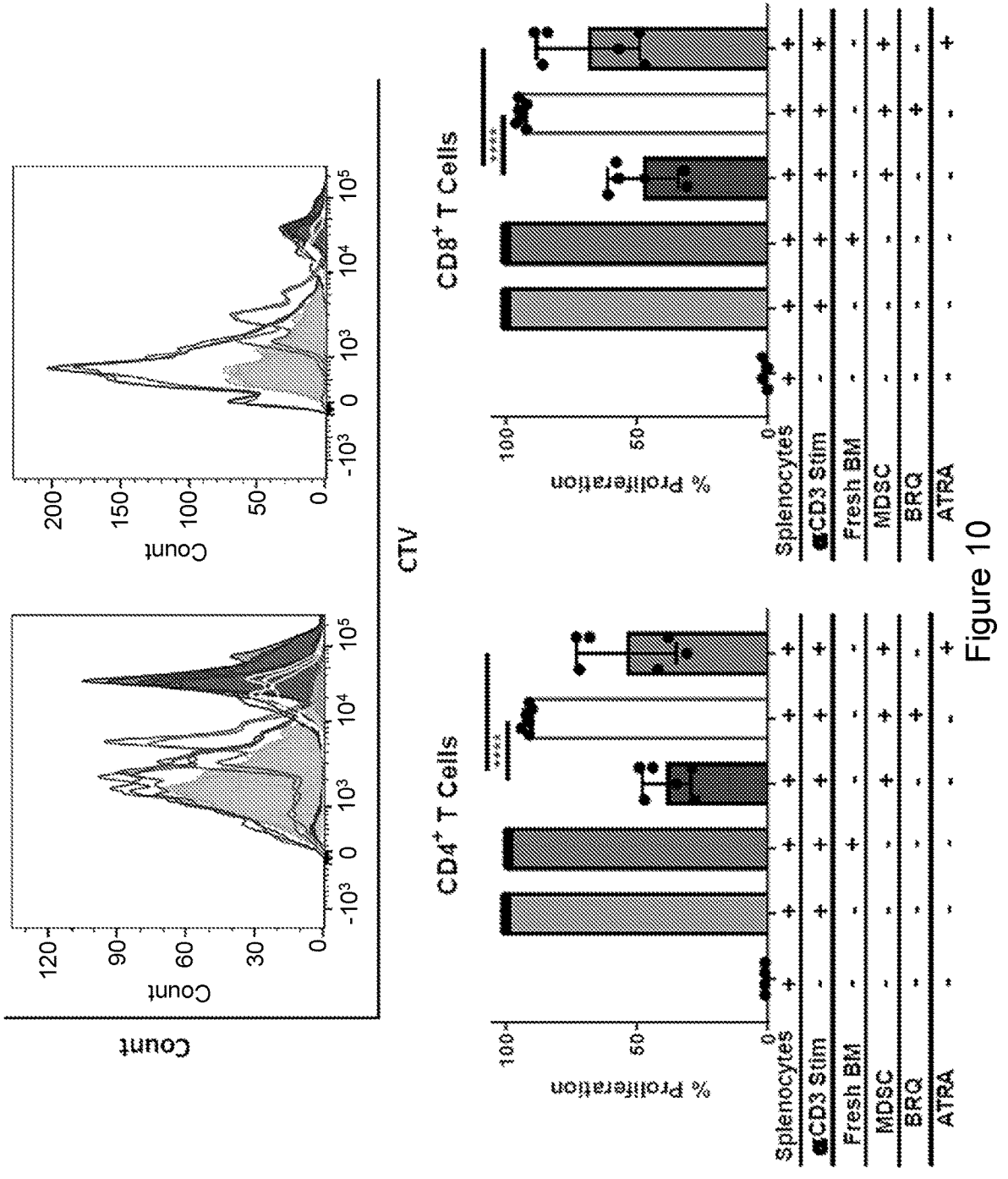

FIGS. 9 and 10. BRQ Treatment More Effectively Reverses Suppression when Compared with ATRA In Vitro. Methods were similar to FIG. 6, except that MDSCs were now generated in vitro with or without (vehicle) concurrent addition of brequinar (BRQ) (1 µM) or all-trans retinoic acid (ATRA; 10 µM) at the start of the culture. Cells were collected for determination of MDSC suppressive activity. The scheme is shown in FIG. 9. FIG. 10 mitigation of the generation of suppressive MDSCs for BRQ and ATRA.

Figure 11:
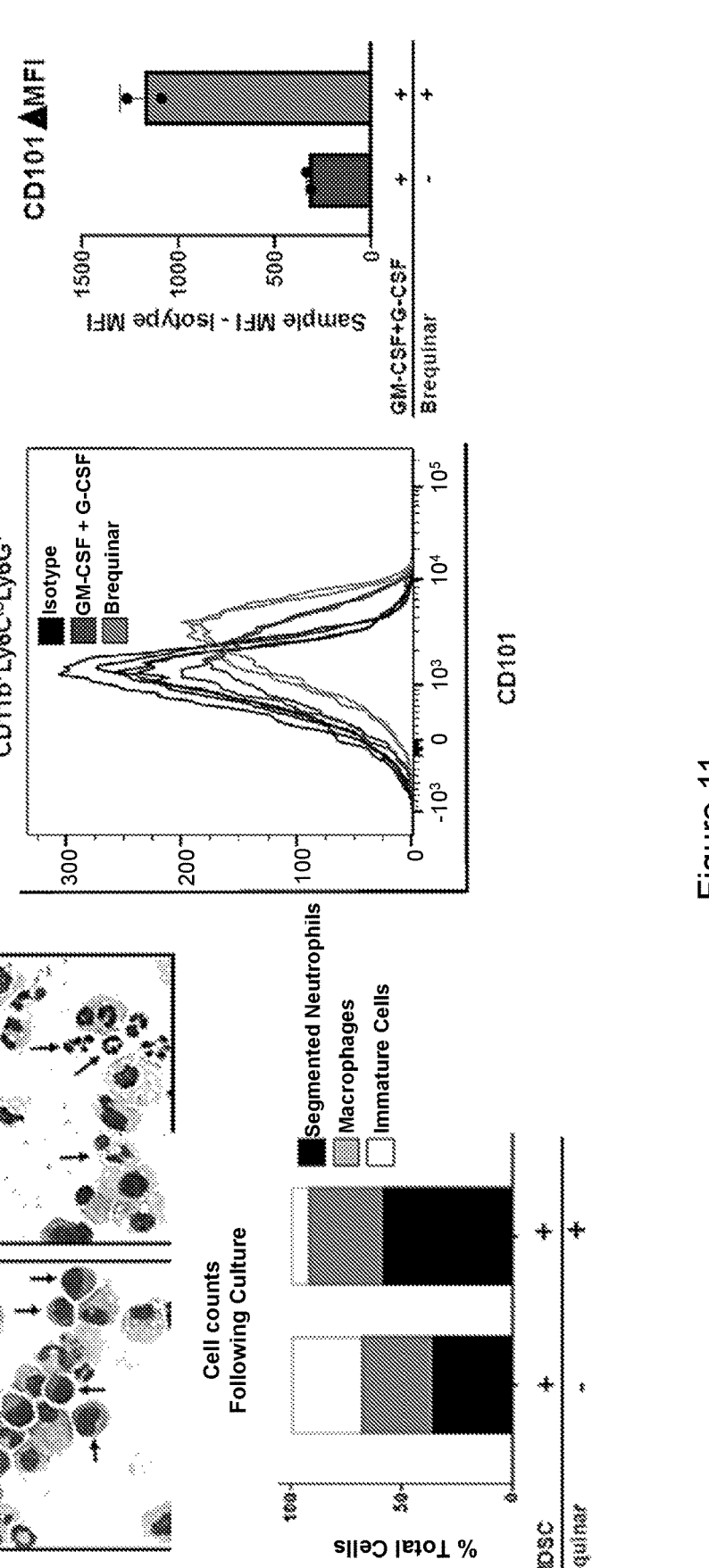

FIG. 11. Cells Treated with BRQ Appear More Mature Morphologically and Phenotypically. Cells were generated in vitro with or without BRQ. Afterwards, cells were collected and analyzed morphologically by Wright-Giemsa staining of cytospin-prepared slides. Left top panel, representative photomicrograph images [arrows indicate representative immature myeloid (−BRQ) vs. mature (+BRQ) cell types)]; Left bottom panel, the % of each cell type was quantified as follows. Cells were classified into 3 main morphologic cell types, as shown. The CD11b$^+$Ly6C$^{lo}$Ly6G$^+$ subset (also known as PMN-MDSCs) was analyzed for cell surface CD101 expression by flow cytometry on cultures without BRQ (labeled here as 'GM-CSF+G-CSF') or with BRQ. Isotype control staining was included as a negative control for the specificity of CD101 reactivity. Middle panel, representative histogram; right panel, mean fluorescence intensity (MFI) data quantified from 2 separate experiments.

Figure 12:
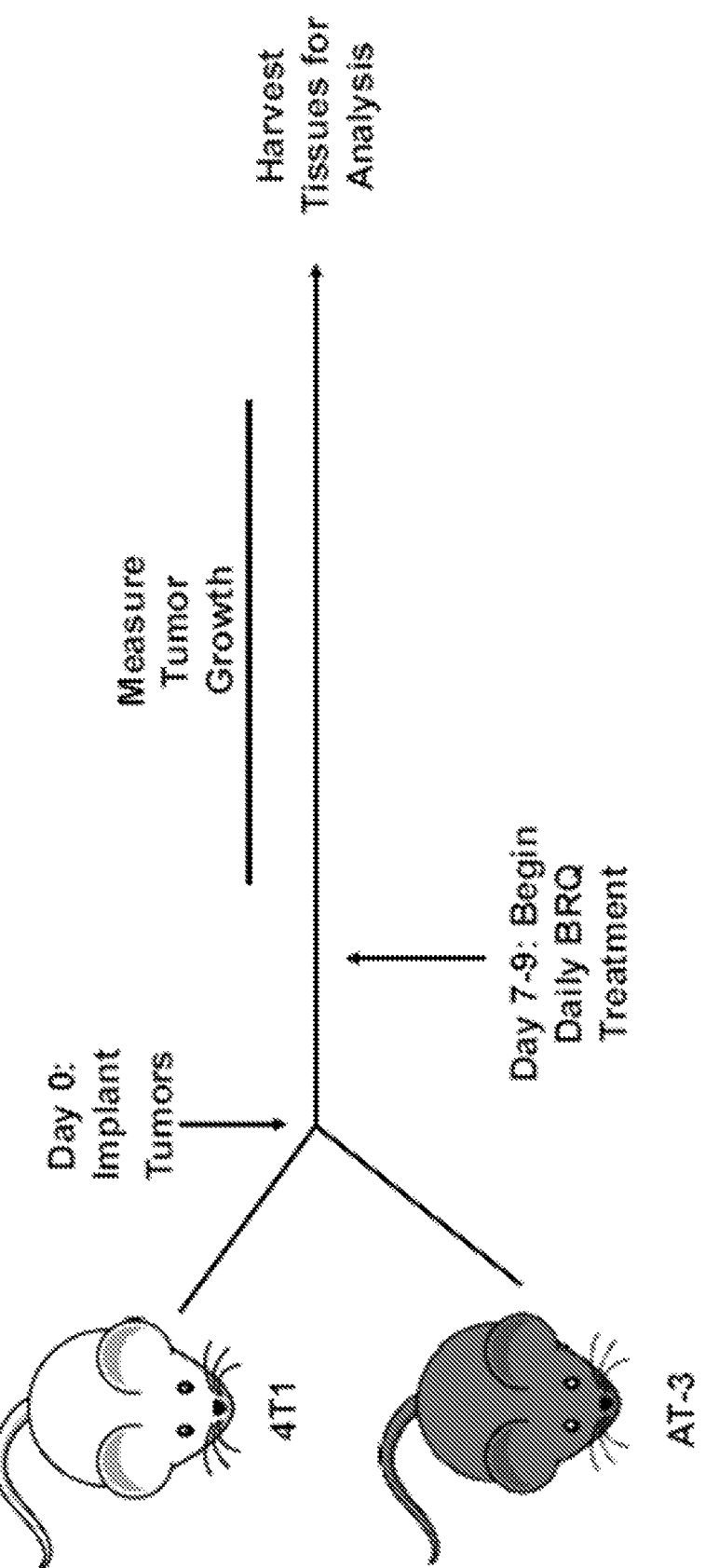

FIGS. 12-15. Treatment of Tumor-Bearing Mice Alters Surface Phenotype of Myeloid Cells. FIG. 12 shows the scheme for testing BRQ in tumor-bearing mice. Female BALB/c or C57BL/6 mice were orthotopically implanted with 4T1 or AT-3 mammary tumor cells, respectively, and were monitored 3 times weekly for tumor growth. When tumors became measurable (indicated by the arrow), BRQ was administered daily. Cells were processed for flow cytometric analysis for the expression (i.e., percentage or MFI value) of the indicated cell surface markers (FIGS. 13-15) and tumor growth was recorded at the time points shown in FIG. 13 (top left panel).

FIGS. 16 and 17. Treatment of Tumor-Bearing Mice Alters Surface Phenotype of Myeloid Cells. Female C57BL/6 mice were orthotopically implanted with AT-3 tumor cells and were monitored 3 times weekly for tumor growth. When tumors became measurable, BRQ was administered daily (10 mg/kg intraperitoneally), and at endpoint the spleens were collected, and the cells processed for flow cytometry for the indicated cell surface markers. Tumor growth is shown in the upper panel of FIG. 16 while representative flow cytometry data is shown in the lower panel. Quantitative data is shown in FIG. 17.

Figure 18:
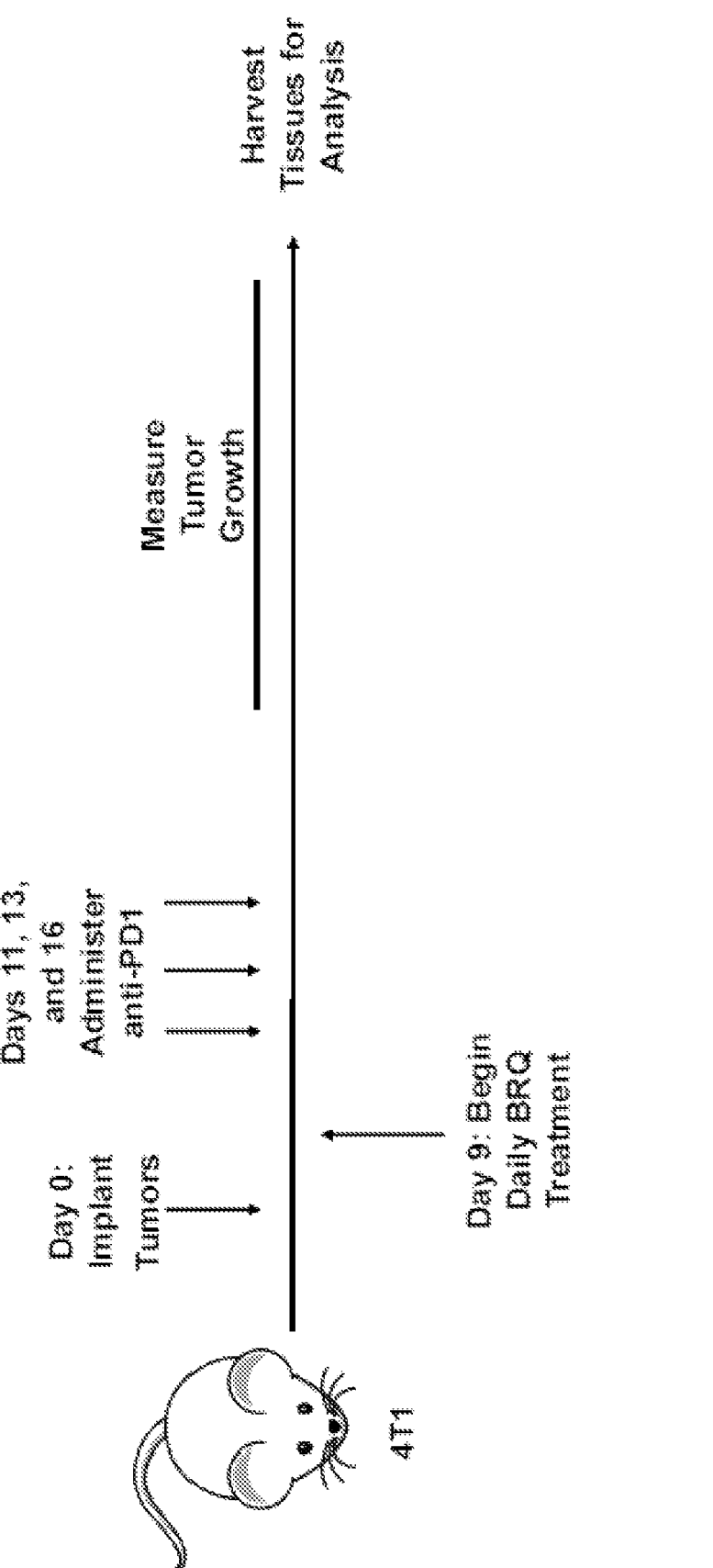

FIGS. 18-20. Effect of Treatment of Tumor-Bearing Mice with BRQ on the Efficacy of Anti-Tumor Immunotherapy. The scheme is shown in FIG. 18. Female BALB/c mice were orthotopically implanted with 4T1 tumors cells and treated with or without BRQ and/or anti-PD-1 monoclonal antibody (mAb) (200 µg given intraperitoneally) at the indicated time points. At endpoint, BM cells or spleens were collected and analyzed for the indicated populations by flow cytometry (FIG. 19). Analysis of the impact of BRQ on T cell numbers and their activation/memory state is shown in FIG. 20.

FIG. 21. Treatment of Tumor-Bearing Mice with BRQ Increases the Proliferative Capacity and Activation of Intra-Tumoral T Cells. Experimental design is same as in FIG. 12.

At endpoint, tumor tissues were collected to produce single cell suspensions for the analyses of the indicated T cell subpopulations expressing the indicated cell surface or intracellular markers by flow cytometry.

Figure 22:
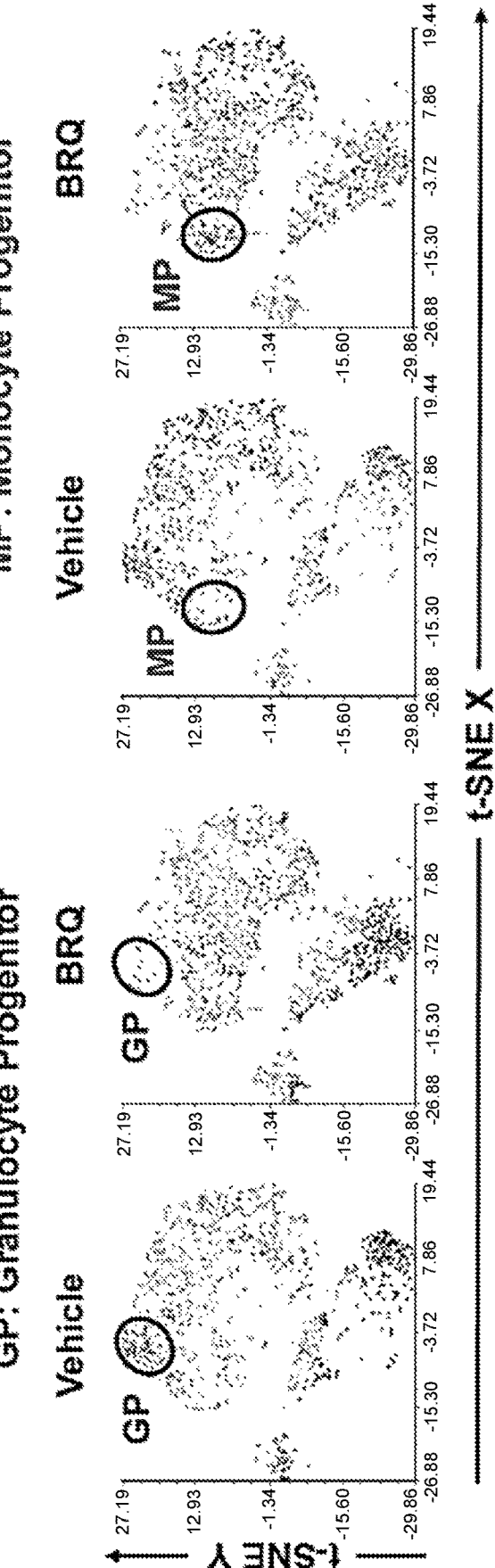

FIG. 22. BRQ Alters the Bone Marrow Myeloid Compartment in a Triple Negative Breast Cancer Model. The experimental design is as described in FIG. 12, but in a different mammary tumor model, termed E0771. Bone marrow cells were collected at endpoint and processed for flow cytometric analysis. Circled regions refer to the data of interest.

Figure 23:
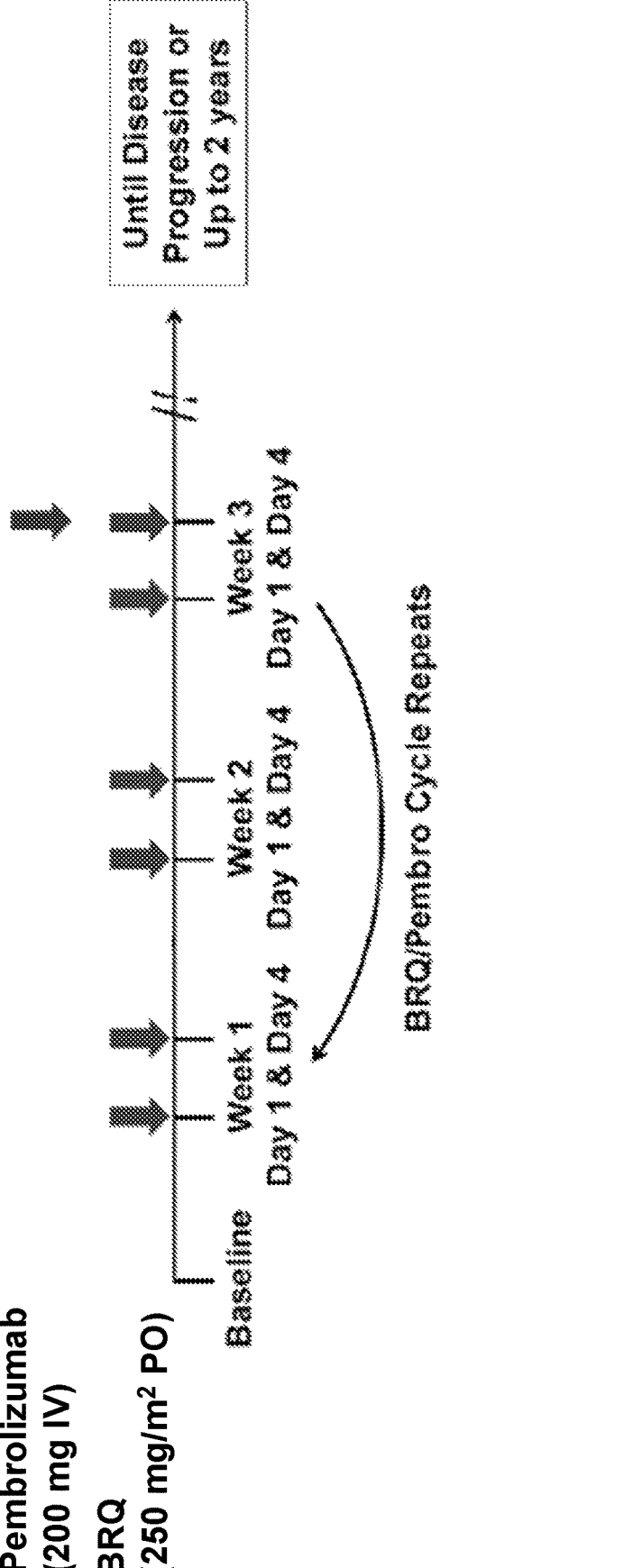

FIG. 23. Illustration of a treatment regimen with BRQ and anti-PD-1. Treatment can be carried out as illustrated in the figure.

DESCRIPTION OF THE DISCLOSURE

The present disclosure provides compositions and methods for treatment of cancer based on improved methods for MDSC depletion. The method for improving MDSC depletion (reducing MDSC burden) may be used by itself or in conjunction with other anti-cancer therapies, including immune-based therapies.

Throughout this application, the use of the singular form encompasses the plural form and vice versa. For example, "a", or "an" also includes a plurality of the referenced items, unless otherwise indicated.

Where a range of values is provided in this disclosure, it should be understood that each intervening value, and all intervening ranges, between the upper and lower limit of that range is also included, unless clearly indicated otherwise. The upper and lower limits from within the broad range may independently be included in the smaller ranges encompassed within the disclosure.

The term "therapeutically effective amount" as used herein refers to an amount of an agent sufficient to achieve, in single or multiple doses, the intended purpose of treatment. Treatment does not have to lead to complete cure, although it may. Treatment can mean alleviation of one or more of the symptoms or markers of the indication. The exact amount desired or required will vary depending on the particular compound or composition used, its mode of administration, patient specifics and the like. Appropriate effective amount can be determined by one of ordinary skill in the art informed by the instant disclosure using only routine experimentation. Within the meaning of the disclosure, "treatment" also includes prophylaxis and treatment of relapse, as well as the alleviation of acute or chronic signs, symptoms and/or malfunctions associated with the indication. Treatment can be orientated symptomatically, for example, to suppress symptoms. It can be effected over a short period, over a medium term, or can be a long-term treatment, such as, for example within the context of a maintenance therapy. Administrations may be intermittent, periodic, or continuous.

In an aspect, this disclosure provides a method for treatment of cancer, such as blood cancer or solid tumor comprising administering to an individual in need of treatment, an agent which reduces MDSC burden (e.g., BRQ or derivative or similar agent in its class known as DHODH inhibitors), alone or in combination with anti-cancer therapy. MDSC burden may be the number of MDSCs. MDSC burden may be the functioning of the MDSCs. The method of treatment of solid tumor or blood cancer may comprise administering to an individual in need of treatment, an agent which reduces MDSC burden in combination with one or more immune checkpoint inhibitors. This disclosure also provides a method for treating cancer metastases comprising administering to an individual in need of treatment, an agent which reduces MDSC burden (e.g., BRQ or derivative or other DHODH inhibitors), alone or in combination with anti-metastatic therapy. The method of treatment of metastases may comprise administering to an individual in need of treatment, an agent which reduces MDSC burden in combination with one or more immune checkpoint inhibitors.

The present disclosure provides a method for altering granulocyte to monocyte ratio in a cancer patient to a ratio that is similar to that from a normal (non-cancer bearing) control. The method comprises administering to an individual in need of treatment, an agent which reduces MDSC burden, alone or in combination with anti-cancer therapy. The method of normalizing the granulocyte to monocyte ratio may comprise administering to an individual in need of treatment, an agent which reduces MDSC burden in combination with one or more immune checkpoint inhibitors. MDCS burden may be calculated as the number of MDSCs per ml of the white blood cell (WBC) fraction or it may be expressed as the number of MDSCs per ml of peripheral blood mononuclear cell (PMBC) fraction. Alternative, MDSC burden may be calculated as the MDSC fraction of the total number of cells in the blood, or WBCs or PMBCs. In general, MDSCs are not detectable or are at very low levels in normal individuals (e.g., cancer-free individuals). MDSCs may be up to 1.5% of total cells in the blood of normal individuals. Their numbers can increase to 10 to 20% or more of total cells in cancer.

An agent for reducing MDSC burden may be one that induces myeloid differentiation of early multipotent progenitors. An example is Brequinar (BRQ), a small molecule inhibitor for inducing myeloid differentiation of early multipotent progenitors. While not intending to be bound by any particular theory, it is considered that this approach will redirect early myeloid precursors away from MDSCs thereby reducing MDSC burden. MDSCs comprise two major subsets: monocytic (M-MDSCs) or polymorphonuclear (PMN-MDSCs), which are related to monocytes or granulocytes, respectively. In cancer, both subsets are arrested at immature states and fail to function properly, acquiring immune suppressive, rather than immune activating, traits and resulting in pro-tumorigenic functions. MDSCs also produce factors that facilitate metastasis by stimulating tumor invasion and angiogenesis. In human cancers, high percentages of circulating MDSCs correlate with poorer outcomes, and their accumulation is thought to reduce the efficacy of both chemotherapies and immunotherapies, including immune checkpoint blockade (ICB). In the present method, in an embodiment, a reduction in MDSC burden is achieved by using an inhibitor that targets early myeloid progenitor common to both MDSC subsets. This strategy differs from others, that are thought to act at more committed stages (such as by using all-trans-retinoic acid (ATRA)), and contrasts with approaches to deplete circulating MDSCs (such as by using 5-fluorouracil (5-FU) or gemcitabine).

An example of an agent useful in the present method for reducing MDCS burden is Brequinar (BRQ), or derivatives thereof. BRQ (6-Fluoro-2-(2'-fluoro-[1,1'-biphenyl]-4-yl)-3-methylquinoline-4-carboxylic acid) is a small molecule inhibitor that forces differentiation of myeloid progenitors, such as GMPs, into mature myeloid populations. BRQ is commercially available (such as from Sigma, R&D Systems, Cayman Chemicals etc.). BRQ is considered to block the enzyme dihydroorotate dehydrogenase (DHODH), which is involved in pyrimidine biosynthesis. A derivative of BRQ suitable for the present method will exhibit the same or similar DHODH inhibitor activity as BRQ. Exemplary derivatives include BAY2402234 (Bayer), AG-636 (Agios Pharmaceuticals, Inc.), Leflunomide or teriflunomide, IMU-838 (Immunic AG), Vidofludimus Calcium, ASLAN003 (Aslan Pharmaceuticals), and PP-001 (Panoptes Pharma GmbH). Other DHODH inhibitors may also be identified that force differentiation of early myeloid precursors, such as GMPs, into mature myeloid populations thereby reducing MDSC numbers.

BRQ or its derivatives may be present as free or as a pharmaceutically acceptable salt thereof (such as mono- or di-salt), such as, for example as sodium, calcium, magnesium or barium salt. The agent may be sodium brequinar. It may also be provided as a prodrug. BRQ or its derivatives may be used at therapeutically effective concentrations. Generally, an amount of from 1 µg/kg to 100 mg/kg and all values therebetween may be used. In an embodiment, 1 $mg/m^2$ to 5000 $mg/m^2$ (e.g., given orally) may be used. In an embodiment, 5 $mg/m^2$ to 500 $mg/m^2$ (e.g., given orally) may be used.

Immune based therapies that may be used in the combination therapy (e.g., in combination with BRQ), include immune checkpoint inhibitors (e.g., anti-PD-1, anti-PD-L1, anti-CTLA-4, etc.), vaccines (e.g., dendritic cell-based; viral-based; autologous whole tumor cell), adoptive cellular therapy (e.g., TILs; T cell receptor-engineered lymphocytes; CAR T cells or CAR NK cells).

Administration of BRQ can be carried out in combination with other cancer therapies including T cell-based immunotherapeutics (including, but not limited to, immune checkpoint inhibitors, adoptive T cell transfer therapy, or cancer vaccines). For example, the PD-1 pathway may be targeted. The programmed death receptor 1 (PD-1) is a T-cell surface receptor that is expressed on T cells, B cells, natural killer cells (NK), activated monocytes and dendritic cells. The role of PD-1 in normal human physiology is to limit autoimmunity by acting as a co-inhibitory immune checkpoint expressed on the surface of T cells and other immune cells, including tumor-infiltrating lymphocytes. It has two ligands: programmed death receptor ligand 1 (PD-L1/B7-H1) and 2 (PD-L2/B7-DC). Examples of T cell-based immunotherapies include adoptive cell transfer therapies in which patients are infused with their own immune cells (e.g., T cells include enriched populations of tumor-reactive T cells, genetically-engineered CAR-T cells (chimeric antigen receptor T cells) or T cell receptor-engineered T cells, and natural killer cells (NK cells; FATE-NK100)); cancer vaccines including dendritic cell (DC)-based vaccines; or antibody therapies directed against immune checkpoints PD-1 (e.g., nivolumab, pembrolizumab, cemiplimab, pidilizumab, PDR001, MEDI4736/duralumab, ABBVI-181), PD-L1 (e.g., atezolizumab, durvalumab, avelumab), CTLA-4 (e.g., ipilimumab, tremelimumab), LAG-3 (e.g., TSR-033), Tim-1 (e.g., TSR-022), or immune-activating antibodies (e.g., directed against 41BB (e.g., utomilumab); Ox40 (e.g., PF-04518600, ABBV-368); and CD122 (e.g., NKTR-262, NKTR-214). Generally, a therapeutically effective amount of an antibody or a composition described herein can be in the range of 0.1 mg/kg to 100 mg/kg and all values therebetween. For example, it can be 0.1 mg/kg to 50 mg/kg. Dosages may alternative given as $mg/m^2$. For example, antibody may be given at a dose of 0.1 $mg/m^2$ to 100 $mg/m^2$.

For the treatment of cancer (such as solid tumors) and/or cancer metastases, BRQ may be used alone or in combination with an anti-cancer therapy as described herein. For example, BRQ may be used in combination with immune checkpoint inhibitors, adoptive T cell transfer therapy, cancer vaccines, surgical resection, radiation etc. BRQ may be used in combination with immune checkpoint inhibitors.

BRQ, alone or in combination with immune checkpoint inhibitors, adoptive T cell transfer therapy, cancer vaccines, surgical resection, radiation etc. may be used in the treatment of metastases, with or without treatment of primary tumors.

The two agents—reducer of MDSC burden, and immune checkpoint inhibitor may be administered in separate compositions or in the same composition, via the same route or separate routes, over a same period of time or different periods of time. The two administrations regimens may overlap partially or completely or not at all. The compositions may comprise a pharmaceutically acceptable carrier or excipient, which typically does not produce an adverse, allergic or undesirable reaction when administered to an individual, such as a human subject. Pharmaceutically acceptable carrier or excipient may be fillers (solids, liquids, semi-solids), diluents, encapsulating materials and the like. Examples include, but are not limited to, saline, buffered saline, dextrose, water, glycerol, ethanol etc.

In an embodiment, the present disclosure provides a method for treatment of cancer, such as a solid tumor, comprising administering to an individual who is afflicted with a solid tumor, an effective amount of a combination of BRQ and anti-PD-1 therapy, such as, for example, nivolumab, pembrolizumab, cemiplimab, pidilizumab, wherein the anti-tumor effect of the combination is greater than the effect of each by itself. The amount of BRQ may be 1 mg/m$^2$ to 5000 mg/m$^2$ (e.g., given orally) and the amount of PD-1 antibody may be 40 mg to 1000 mg, which may be administered every three weeks. For example a dose of about 200 mg may be given iv every 21 days.

The two therapies may be administered in a continuous manner or intermittently and may be sequential or overlapping. The treatment regimens can be varied by the treating physician. An example of a treatment regimen is provided in FIG. 23.

The pharmaceutical compositions may be in the form of solutions, suspensions, emulsions, and solid injectable compositions that are dissolved or suspended in a solvent immediately before use. The injections may be prepared by dissolving, suspending or emulsifying one or more of the active ingredients in a diluent. Examples of diluents are distilled water for injection, physiological saline, physiologic buffer, vegetable oil, alcohol, and a combination thereof. Further, the compositions may contain stabilizers, solubilizers, suspending agents, emulsifiers, soothing agents, buffers, preservatives, etc. The pharmaceutical compositions may be formulated into a sterile solid or powdered preparation, for example, by freeze-drying, and may be used after sterilized or dissolved in sterile injectable water or other sterile diluent(s) immediately before use. The compositions can include one or more standard pharmaceutically acceptable carriers. Some examples herein of pharmaceutically acceptable carriers can be found in: Remington: The Science and Practice of Pharmacy (2013) 22nd Edition, Pharmaceutical Press.

The pharmaceutical composition of the invention may be administered via any route that is appropriate, including but not limited to oral, parenteral, sublingual, transdermal, rectal, transmucosal, topical, via inhalation, via buccal administration, or combinations thereof. Parenteral administration includes, but is not limited to, intravenous, intraarterial, intraperitoneal, subcutaneous, intratumoral, intramuscular, intrathecal, and intraarticular. The agents(s) can also be administered in the form of an implant, which allows a slow release of the compound(s), as well as a slow controlled i.v. infusion. BQR or its derivative, and the immune checkpoint inhibitor may be delivered via different routes.

Individuals who may receive the combination treatment described herein include those afflicted with or diagnosed with any type of cancer. Examples include cancers where MDSCs are induced. Examples include any type of malignant solid tumor. Examples include but are not limited to, breast cancer, lung cancer, which may be non-small cell lung cancer (NSCLC). The NSCLC may be squamous cell (or epidermoid) carcinoma, adenocarcinoma and, large cell (or undifferentiated) carcinoma, or any other type, melanoma of the skin, kidney cancer, bladder cancer, liver cancer, pancreatic cancer, colon cancer, colorectal, cervical, gastric, ovarian, head and neck cancers, and Hodgkin lymphoma, other urinary tract cancers, and other types of cancers. BRQ or the combination of BRQ and immune checkpoint inhibitor can be used for the treatment of breast cancer including all stages. Breast cancer may be refractory to current treatments. The breast cancer may be metastatic triple-negative breast cancer, all stages, and may be refractory to current treatments. Breast cancer may be of any subtype, such as, for example, hormone-receptor-positive or ER–/Her2+.

Evaluation of the effectiveness of the treatments as described herein may be carried out based on monitoring the tumor size or other related symptoms, or by monitoring the granulocyte to monocyte ratio, or MDSC burden. In an embodiment, a method is provided to monitor the effectiveness of BRQ or a derivative thereof by periodically evaluating the granulocyte to monocyte ratio. A reduction in the ratio after initiation of the treatment is an indication of the effectiveness of the treatment.

In an aspect, this disclosure provides compositions for the treatment of cancer. The composition comprises an agent that can reduce MDCS burden and an immune checkpoint inhibitor. The composition can comprise i) BRQ and/or a derivative thereof, and ii) a monoclonal antibody directed to PD-1 pathway.

In an aspect, this disclosure provides kits for the treatment of cancer. The kit may comprise in single or separate compositions: i) BRQ and/or a derivative thereof, and ii) an immune checkpoint inhibitor. Buffers and instructions for administration may also be provided. In an embodiment, the kit may comprise single or separate compositions: i) BRQ and/or a derivative thereof, and ii) anti-PD-1 antibody, such as nivolumab, pembrolizumab, cemiplimab, pidilizumab.

The following example is provided to illustrate the invention and is not intended to be restrictive.

Example 1

This example describes studies to test the efficacy of BRQ at inhibiting tumor growth in the 4T1 model, which is refractory to immune checkpoint blockade (ICB). BRQ or anti-PD-1 alone had little effect on tumor growth (FIG. 1A, two separate experiments). However, BRQ plus anti-PD-1, which requires functional cytotoxic T cells, led to significant antitumor and anti-metastatic effects (FIG. 1A, B). Moreover, BRQ alone or combined with anti-PD-1, but not anti-PD-1 alone, significantly altered the granulocyte to monocyte ratio resembling the non-tumor-bearing controls (FIG. 1C). This 'normalization' of the granulocytic/monocytic ratio indicates a reduction in MDSC load. These data further suggested that single-agent BRQ was not directly tumoricidal in vivo. In our model and under these conditions, we found that BRQ plus anti-PD-1 mediated strong antitumor activity (FIG. 1A, B), further suggesting efficient T cell trafficking to the TME. BRQ did not alter CD3$^+$ T cell numbers or the ability of CD8$^+$ T cells to form memory populations in tumor-bearing mice relative to the tumor-free controls (1D, E). These data suggest that BRQ is not having significant off-target effects on T cells.

Data also showed that BRQ was more effective than ATRA in limiting the formation of immune suppressive cells in vitro (FIG. 2A). The BRQ target DHODH is involved in pyrimidine biosynthesis and exogenously supplied uridine blocked the effect of BRQ (FIG. 2B), consistent with inhibition of DHODH and pyrimidine depletion as the mechanism of action of BRQ. As expected from the decrease in MDSC activity (FIG. 2A, B) and the normalization of the granulocytic to monocytic ratio in tumor-bearing mice (FIG. 1C), we observed an increase in IRF8 expression in bone marrow cells cultured with BRQ (FIG. 2C) and a 75% reduction in immature myeloid cells with a corresponding increase in mature myeloid cells (mainly neutrophils and macrophages), based on morphologic analyses. Thus, these data suggest that by changing the cellular metabolism, BRQ enables IRF8 expression, and increased IRF8 shifts differentiation from MDSCs toward mature myeloid populations. Interestingly, this increase in IRF8 was associated with a reciprocal decrease in SLFN4 expression.

To identify or confirm that BRQ inhibits the development of human MDSCs, Lin$^-$bone marrow cells can be isolated from patients and in the case of breast cancer, from female age-appropriate healthy donors and the cells can be cultured with MDSC-inducing cytokines in the presence or absence of BRQ. Myeloid outcomes can be monitored, including PMN-MDSCs and M-MDSCs at phenotypic, morphologic, and functional levels for suppressive activity. We have successfully generated suppressive cells in vitro from human donors (FIG. 3). PMN-MDSCs can be defined as CD11b$^+$CD33$^+$CD14$^-$CD15$^+$HLA-DR$^-$; M-MDSCs can be defined as CD11b$^+$CD33$^+$CD14$^+$CD15$^-$HLA-DR$^{lo}$/−. If the purity of the resultant culture is <90%, cells expressing these MDSC phenotypes can be isolated by flow cytometric sorting. The unfractionated bone marrow cells can serve as a source of autologous T cells for testing the suppressive activity of the induced MDSCs. T cells within the bone marrow can be isolated by magnetic bead separation and stimulated with anti-CD3/anti-CD28 beads in the absence or presence of the induced MDSCs using multiple MDSC to T cell ratios.

Example 2

This example provides additional data to illustrate the invention.

In Vitro Development of MDSCs. Unfractionated mouse bone marrow cells were cultured in dishes with recombinant mouse G-CSF and recombinant mouse GM-CSF (40 ng/ml of each cytokine) for 96 hours to produce MDSCs, as described (Marigo et al. Immunity 32:790-802, 2010). After culture, cells were collected and analyzed by flow cytometry for the indicated cell surface markers. Uncultured or fresh bone marrow (BM) cells served as a negative control. Results shown in FIG. 4 indicate that BM cells cultured under these conditions exhibit a robust increase in the gated (i.e., upper right-boxed quadrant) CD11b$^+$Gr-1$^+$ cells, a canonical phenotype characteristic of mouse MDSCs. Functional assessment was performed as shown in FIG. 5.

Cultured Cells Develop Potent Immunosuppressive Capacity. Using the methods described for FIG. 4, experiments were then performed to determine whether the cells generated from this BM culture system functionally behaved as MDSCs, based on their ability to inhibit T cell proliferation in vitro. To that end, fresh BM (i.e., no in vitro culture) or cultured BM cells (i.e., MDSCs at two different MDSC-to-T cell ratios of 1:1 or 1:2) were co-mixed in 96-well plates with CellTrace Violet (CTV)—stained syngeneic naïve splenocytes as a source of T cells and stimulated with or without soluble agonistic anti-CD3 monoclonal antibody (mAb) (1 μg/ml) for 72 hours. After co-culture, CTV dye dilution in the gated CD4$^+$ or CD8$^+$ T cell fractions within the splenocyte populations was analyzed by flow cytometry to determine the extent of proliferation based on dye dilution. In FIG. 5, top panels show CTV dye dilution, as determined by flow cytometry and depicted as a histogram; bottom panels indicate the percentage of proliferation, based on quantification of the histogram data. Left side, CD4$^+$ T cell proliferation; right side, CD8$^+$ T cell proliferation. Shades shown in histogram correspond to colors shown in bar graph. Asterisks refer to significant differences. Each data point represents a technical replicate. MDSCs generated using this BM culture system displayed a significant ability to inhibit CD4$^+$ or CD8$^+$ T cell proliferation at two different myeloid-to-splenocyte ratios, as measured by a reduction in the percentage of proliferation. Splenocytes incubated without anti-CD3 mAb did not proliferate (indicated as 0%), while splenocytes incubated with anti-CD3 mAb proliferated robustly (indicated as 100%). This validates the success of developing an in vitro MDSC assay to investigate subsequent questions about MDSC biology, namely the impact of targeted therapies or agents on MDSC development or function.

Effect of BRQ Treatment on In Vitro Generated MDSCs. As in FIG. 4, MDSCs were generated in vitro, but now with or without (vehicle) the concurrent addition of brequinar (BRQ) (1 μM) at the start of the culture. After culture, cells were collected and analyzed by flow cytometry for the indicated cell surface markers. Uncultured (fresh) BM cells served as a negative control. Viable cells were enumerated by trypan blue dye exclusion (bottom left panel, % viability; bottom right panel, total viable cells recovered). Results are shown in FIG. 6. Similar to FIG. 4, BM cells cultured under these conditions exhibited a robust emergence or accumulation of CD11b$^+$Gr-1$^+$ cells. The inclusion of BRQ to the culture system did not substantially alter the generation of these CD11b$^+$Gr-1$^+$ cells, based on flow cytometry depicted as a dot plot on the gated (upper right-boxed quadrant) cells. Interestingly, while cell viability was not significantly altered by BRQ treatment, the number of live cells recovered was substantially reduced, consistent with a cytostatic effect.

BRQ Treatment Significantly Reverses the Immune Suppressive Capacity of MDSCs. The methods used were the same as for FIG. 5 for details of the suppression assay and the methods used to analyze T cell proliferation, except that an additional group with BRQ (1 μM) was included, as described in the experiment for FIG. 6. Results are shown in FIG. 7. Cells produced as described for FIG. 6, were then assayed for their ability to inhibit T cell proliferation (tested at myeloid cell-to-splenocyte ratio of 1:1). Indeed, MDSCs generated in the absence of BRQ displayed a potent ability to inhibit CD4$^+$ or CD8$^+$ T cell proliferation. However, the addition of BRQ to the culture system significantly reduced the ability of these in vitro-generated MDSCs to inhibit T cell proliferation, compared to the controls incubated without any myeloid cells or fresh BM cells as another negative control.

Supplementation with Uridine Rescues the Effects of BRQ Treatment. Suppression assay and the methods used to analyze T cell proliferation were the same as described above, except that an additional group with BRQ (1 μM) plus extracellular uridine (200 μM) was included. NS refers to not significant. Results are shown in FIG. 8. One approach to antagonizing or blocking the effects of BRQ is by increasing the availability of extracellular uridine in the environment or milieu. First, as seen earlier in FIGS. 5 and 7, CD4$^+$ or CD8$^+$ T cell proliferation is inhibited by MDSCs. Second, as seen earlier in FIG. 7, the addition of BRQ mitigates MDSC suppressive activity, as T cell proliferation is significantly restored. And third, the addition of uridine antagonized the effect of BRQ and restored MDSC suppressive activity, as measured by a reduction in T cell proliferation. This experiment with uridine supplementation served as an important specificity control of the mechanism of action of BRQ.

BRQ Treatment More Effectively Reverses Suppression when Compared with ATRA In Vitro. Methods were similar to FIG. 6, except that MDSCs were now generated in vitro with or without (vehicle) concurrent addition of brequinar (BRQ) (1 μM) or all-trans retinoic acid (ATRA; 10 μM) at the start of the culture. After culture, the cells were collected for determination of MDSC suppressive activity. The scheme, shown in FIG. 9, is characterized as a form of differentiation therapy for certain subtypes of acute myeloid leukemia (AML), such as APL (acute promyelocytic leukemia). Here, we compared both BRQ and ATRA side-by-side to determine similarities or differences in their ability to block the generation of MDSCs in vitro. The results shown in FIG. 10 indicated that BRQ is more effective than ATRA in its capacity to mitigate the generation of suppressive MDSCs. Cultures containing BRQ were significantly less suppressive to CD4$^+$ or CD8$^+$ T cell proliferation compared to cultures containing ATRA.

Cells Treated with BRQ Appear More Mature Morphologically and Phenotypically. Methods were the same as in FIG. 6. MDSCs were generated in vitro with or without BRQ. Afterwards, cells were collected and analyzed morphologically by Wright-Giemsa staining of cytospin-prepared slides. Left top panel, representative photomicrograph images [(arrows indicate representative immature myeloid (–BRQ) vs. mature (+BRQ) cell types)]; Left bottom panel, the % of each cell type was quantified as follows. Cells were classified into 3 main morphologic cell types, as shown. For the lower panel, 300 cells were analyzed per random field and 3 separate fields were analyzed (totaling 900 cells). The average number of each cell type was determined by dividing by 3, and the data were converted to a percentage within the total population. Using the in vitro assay described previously to produce MDSCs, the CD11b$^+$Ly6C$^{lo}$ Ly6G$^+$ subset (also known as PMN-MDSCs) was analyzed for cell surface CD101 expression by flow cytometry on cultures without BRQ (labeled here as 'GM-CSF+G-CSF') or with BRQ. Isotype control staining was included as a negative control for the specificity of CD101 reactivity. Middle panel, representative histogram; right panel, mean fluorescence intensity (MFI) data quantified from 2 separate experiments. The results shown in FIG. 11 indicated that cultures containing BRQ displayed a more mature phenotype compared to the controls (without BRQ). Morphologic inspection showed that BRQ increased the proportion of segmented neutrophils, consistent with maturation. The increase in segmented neutrophils appears to culminate at the expense of a reduction in immature cell types, although no demonstrable effect was observed on the proportion of macrophages. Moreover, recent work in the field of neutrophil biology has demonstrated that cell surface expression of CD101 is specifically or selectively observed on mature neutrophils, while CD101$^-$ neutrophils are immature and associated with tumor progression. Thus, the impact of BRQ on CD101 expression was investigated on cells recovered from this MDSC culture system and observed that BRQ significantly increased the expression of CD101. Together, these data indicate that BRQ can drive myeloid differentiation/maturation, as assessed by morphology and cell surface marker expression, and that these effects were most observed in the neutrophil population.

Figure 13:
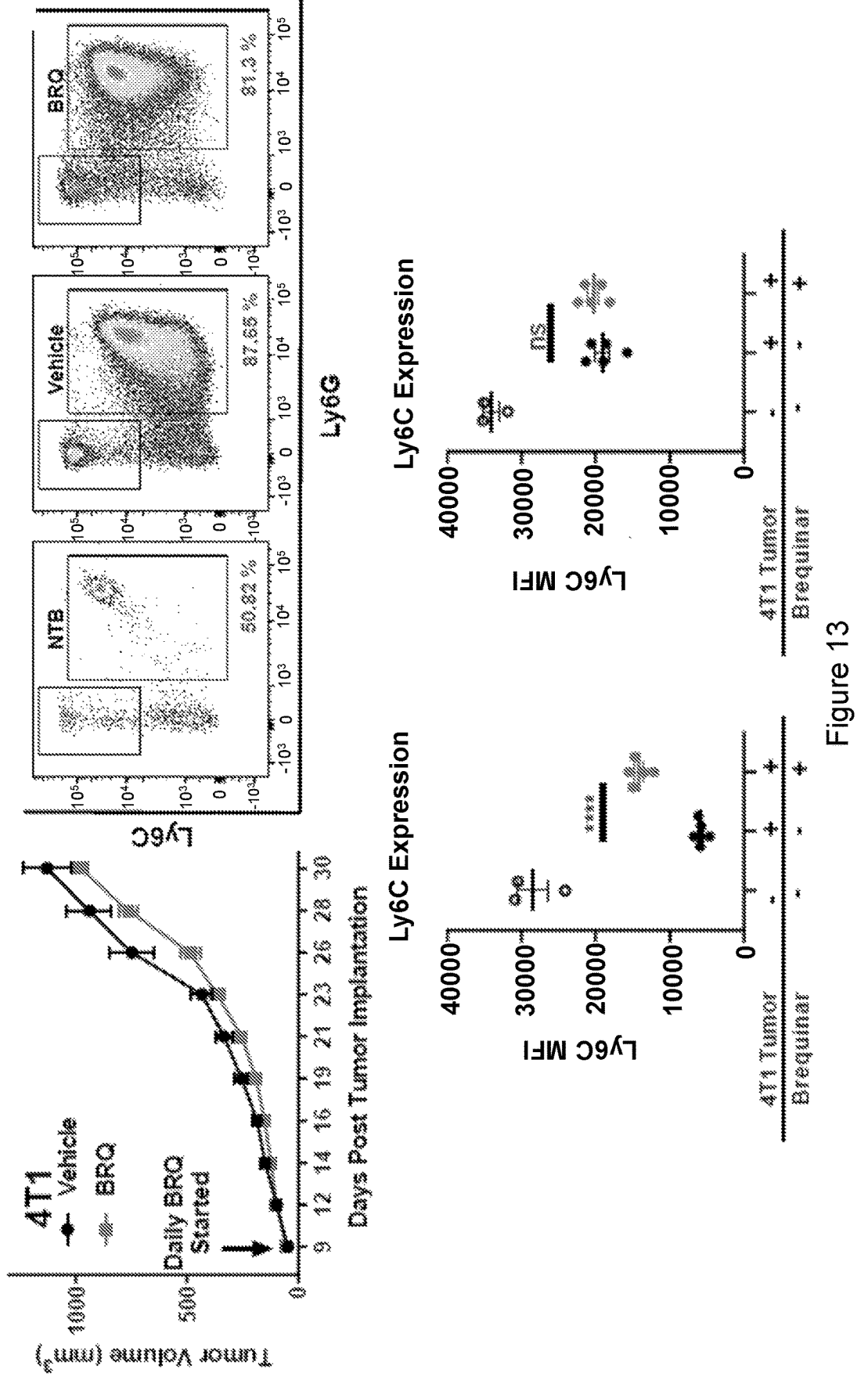

Treatment of Tumor-Bearing Mice Alters Surface Phenotype of Myeloid Cells. FIG. 12 shows the scheme for testing BRQ in tumor-bearing mice. Female BALB/c or C57BL/6 mice were orthotopically implanted with 4T1 or AT-3 mammary tumor cells, respectively, and were monitored 3 times weekly for tumor growth. When tumors became measurable (indicated by the arrow), BRQ was administered daily (10 mg/kg intraperitoneally), and at endpoint the BM cells or spleens were collected for flow cytometric analysis for the expression (i.e., percentage or MFI value) of the indicated cell surface markers (FIGS. 13-15). Tumor growth was recorded at the time points shown in FIG. 13 (top left panel). We extended our in vitro studies with BRQ to in vitro settings to determine the impact of BRQ on MDSC maturation. To that end, mice bearing orthotopically implanted mammary tumors were treated with or without BRQ in vivo using a similarly previously reported dose, frequency and schedule (Sykes et al. Cell 167:171-186, 2016). The first tumor model chosen was 4T1, which is an aggressive mammary tumor cell line that induces a robust MDSC response largely comprised of PMN-MDSCs. Treatment of mice bearing 4T1 tumors with BRQ had only a nominal effect on primary tumor growth and did not significantly alter the accumulation of the granulocytic population, as measured in the spleen (upper right panel; see upper right-boxed quadrant). However, the granulocytic cells generated in mice treated with BRQ had significantly higher expression of the cell surface Ly6C, consistent with a more mature phenotype (see lower left panel; the –/– group refers to non-tumor-bearing control mice). The expression of Ly6G trended upward but did not reach statistical significance (lower right panel). Moreover, BRQ treatment significantly increased CD101 expression on these splenic granulocytic populations, indicating that the myeloid compartment had become more enriched with mature neutrophils.

The upper panels of FIG. 14 are representative flow cytometry plots of the non-tumor-bearing (NTB) or tumor-bearing cohorts without (vehicle) or with BRQ. The middle panel histogram represents CD101 expression on the gated (boxed) populations of the upper panels. In this case, the far-right histograms refer to the gated-boxed right dot plot (for the PMN or granulocytic subset), whereas the gated-boxed left histogram refers to the gated-boxed upper left dot plot (for the monocytic subset). The lower panel (tables) represent the labeling used to identify the different MDSC subsets in the gated-boxed panels. 'Median' refers to the MFI values, indicating that the PMN-MDSC subset has higher CD101 expression values compared to the monocytic subset, which is consistent with the CD101 expression pattern. FIG. 15 refers to the quantification of the CD101 data from non-tumor-bearing mice or tumor-bearing mice with or without BRQ, based on both the CD101 MFI values and the percentages of CD101$^+$ (or high-expressing) cells reflecting the monocytic subset (upper left histogram and middle left table) or the PMN-MDSC subset (upper right histogram and middle right table). The quantification appears in the lower left and right graphs. Each point represents an individual mouse.

In another experiment, the scheme shown in FIG. 12 was used. Female C57BL/6 mice were orthotopically implanted with AT-3 tumor cells and were monitored 3 times weekly for tumor growth. When tumors became measurable, BRQ was administered daily (10 mg/kg intraperitoneally), and at endpoint the spleens were collected and analyzed by flow cytometry for the indicated cell surface markers. Tumor growth is shown in the upper panel of FIG. 16 while representative flow cytometry data is shown in the lower panel. Quantitative data is shown in FIG. 17. Using the AT-3 mammary tumor cell line as a second tumor model, BRQ exerted minimal effects on inhibiting tumor growth, which was comparable with that observed with the 4T1 tumor cell line. Also, as with the 4T1 model, we observed that BRQ treatment of AT-3-bearing mice significantly increased the expression of Ly6C on the granulocytic (PMN-MDSC) subset. Moreover, BRQ treatment increased the expression of Ly6G on the surface of granulocytes. In contrast, no significant changes were observed on the monocytic subset for Ly6C or Ly6G expression, supporting the notion that BRQ has its greatest impact on the dominant PMN-MDSC subset in these tumor-bearing mice.

Effect of Treatment of Tumor-Bearing Mice with BRQ on the Efficacy of Anti-Tumor Immunotherapy. As shown in FIG. 18, Female BALB/c mice were orthotopically implanted with 4T1 tumors cells and treated with or without BRQ and/or anti-PD-1 monoclonal antibody (mAb) (200 μg given intraperitoneally) at the indicated time points, as in FIG. 12. At endpoint, BM cells or spleens were collected and analyzed for the indicated populations by flow cytometry. Results are shown in FIG. 19. These experiments sought to determine whether BRQ can act in the bone marrow environment. BRQ treatment reduced the accumulation of $CD11b^+Gr-1^+$ cells (based on the canonical MDSC phenotype) compared to the vehicle controls (left panel). The frequency of these cells approached levels seen in the non-tumor-bearing controls. Furthermore, single-agent BRQ reduced tumor-driven expansion (indicated as 'NT' for no treatment/vehicle) of two distinct myeloid progenitor populations, granulocyte-monocyte progenitor (GMP) or granulocyte progenitor (GP) (middle and right panels). Anti-PD-1 alone had no effect, although the combination treatment trended toward a decrease. These data are consistent with the hypothesis that BRQ treatment altered the myeloid compartment of the bone marrow microenvironment and reduced the antecedents (i.e., immediate upstream progenitors) to MDSCs. Moreover, analysis of the systemic impact of BRQ on T cell numbers and their activation/memory state was performed on splenic population at endpoint (FIG. 20). The results showed that BRQ treatment had no negative effect on the presence of either total ($CD3^+$) T cells (upper panel) or the ratio of memory to naïve T cells as defined by CD44 surface expression. These data suggested that BRQ was not toxic to T cells in vivo and did not alter their ability to become activated or to differentiate. This analysis at the time was not performed on cohorts treated with anti-PD-1 mAb alone or the combination, since the intent was to focus on the effect of BRQ on T cell numbers and their phenotypic states.

Treatment of Tumor-Bearing Mice with BRQ Increases the Proliferative Capacity and Activation of Intra-Tumoral T Cells. Experimental design is as described in FIG. 12. At endpoint, tumor tissues were collected to produce single cell suspensions for the analyses of the indicated T cell subpopulations expressing the indicated cell surface or intracellular markers by flow cytometry. In the case of IFN-γ expression, T cells were stimulated for 4 hours with 20 ng/ml PMA, 0.83 mg/ml ionomycin and 1.1 mg/ml Brefeldin A prior to analysis by intracellular flow cytometry, a general method used to maximize cytokine production and quantification. The results, shown in FIG. 21, revealed significant increases in the proliferative capacity of both intratumoral $CD8^+$ and $CD4^+$ T cells, as measured by increases in the percentages of $Ki-67^+$ cells in mice treated with either BRQ alone or in combination with anti-PD-1 mAb. Increases in CD44 expression were similarly observed in both T cell subpopulations, consistent with immune activation and/or differentiation into effector or memory phenotypes. Interestingly, $CD8^+$ T cells from mice treated with a combination of BRQ and anti-PD-1 also showed an increased ability to produce IFN-γ.

BRQ Alters the Bone Marrow Myeloid Compartment in Triple Negative Breast Cancer Model. This study was performed in another mammary tumor model, termed E0771. The experimental design is as described in FIG. 12 and bone marrow cells were collected at endpoint, as in FIG. 19 for flow cytometric analysis. Here, BM samples were analyzed by multi-spectral high dimensional flow cytometry using a Cytek Aurora Spectral Flow Cytometer and the data are illustrated as a TSNE plot (i.e, t-distributed Stochastic Neighbor). Circled regions refer to the data of interest. Results are shown in FIG. 22. Using a mammary tumor model, termed E0771, BRQ reduced the frequency of granulocyte progenitors (GPs) and increased the frequency of monocyte progenitors (MPs) in vivo, as measured by multi-spectral flow cytometry, consistent with a normalization of the granulocyte/monocyte ratio we had observed in the periphery (FIG. 1, panel C).

FIG. 23 describes an embodiment in treatment of metastatic triple-negative breast cancer (TNBC) patients receiving the combination of BRQ and anti-PD-1. Treatment can comprise a combination of BRQ and anti-PD-1, reflecting the indicated doses, routes, frequency, and schedule. BRQ can be taken orally twice weekly, while pembrolizumab (or other immune therapy) can be injected iv at 21-day intervals, starting at week 3 post-BRQ treatment and the cycle will continue as shown. At specified pre- and post-treatment time points, blood (PBMCs), serum, and tumor biopsies can be collected for immunologic and molecular studies.

The data presented here demonstrate that BRQ attenuates suppressive MDSC generation in vitro and that BRQ treatment in vivo results in an increasingly differentiated MDSC population and results in a significant improvement in the anti-tumor efficacy of immune checkpoint blockade.

While the invention has been described through embodiments, routine modifications to the disclosure here will be apparent to those skilled in the art. Such modifications are intended to be within the scope of this disclosure.

What is claimed is:

1. A method for alleviation of acute and chronic signs and symptoms associated with a cancer selected from a group consisting of breast, lung, renal, colorectal, cervical, gastric, ovarian, prostate, pancreatic cancer, or melanoma, the method comprising administering an anti-PD-1 antibody to the individual diagnosed with a said cancer, the method further comprising administering brequinar to the individual to inhibit development of myeloid-derived suppressor cells (MDSC) burden by reducing the frequency of granulocyte progenitors and increasing the frequency of monocyte progenitors in bone marrow of the individual.

2. The method of claim 1, wherein the anti-PD-1 antibody is pembrolizumab.

3. The method of claim 2, wherein the breast cancer is triple negative breast cancer.

4. The method of claim 3, wherein the breast cancer is refractory to chemotherapy, hormonal treatment, radiation, or surgical treatment.

5. The method of claim 3, wherein the breast cancer is metastatic triple-negative breast cancer.

6. The method of claim 5, wherein metastasis of the cancer is also inhibited, and wherein the cancer is refractory to immune checkpoint blockade.

\* \* \* \* \*